US009029330B2

(12) United States Patent
Webster et al.

(10) Patent No.: US 9,029,330 B2

(45) Date of Patent: May 12, 2015

(54) METHODS OF TREATING CANCER USING INTERLEUKIN-12P40 VARIANTS HAVING IMPROVED STABILITY

(75) Inventors: Gordon D. Webster, Cambridge, MA (US); Suzanne P. McKenzie, West Newton, MA (US); Kin-Ming Lo, Lexington, MA (US); Pascal André Stein, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 49 days.

(21) Appl. No.: 13/478,897

(22) Filed: May 23, 2012

(65) Prior Publication Data

US 2013/0034518 A1 Feb. 7, 2013

Related U.S. Application Data

(62) Division of application No. 12/961,733, filed on Dec. 7, 2010, now Pat. No. 8,188,248, which is a division of application No. 11/647,661, filed on Dec. 29, 2006, now Pat. No. 7,872,107.

(60) Provisional application No. 60/755,382, filed on Dec. 30, 2005.

(51) Int. Cl.

| | |
|---|---|
| ***A61P 35/00*** | (2006.01) |
| ***H04N 21/61*** | (2011.01) |
| ***H04N 21/462*** | (2011.01) |
| ***H04N 21/8549*** | (2011.01) |
| *C07H 21/04* | (2006.01) |
| *C12N 1/21* | (2006.01) |
| *C12N 5/16* | (2006.01) |
| *C12P 21/04* | (2006.01) |
| *C12N 15/09* | (2006.01) |
| *C07K 14/54* | (2006.01) |
| *C07K 19/00* | (2006.01) |
| *A61K 38/00* | (2006.01) |

(52) U.S. Cl.

CPC ............ *H04N 21/6106* (2013.01); *A61K 38/00* (2013.01); *C07K 14/5434* (2013.01); *H04N 21/462* (2013.01); *H04N 21/8549* (2013.01)

(58) Field of Classification Search

None

See application file for complete search history.

(56) References Cited

U.S. PATENT DOCUMENTS

| | | | |
|---|---|---|---|
| 4,196,265 | A | 4/1980 | Koprowski et al. |
| 4,676,980 | A | 6/1987 | Segal et al. |
| 5,073,627 | A | 12/1991 | Curtis et al. |
| 5,082,658 | A | 1/1992 | Palladino |
| 5,091,513 | A | 2/1992 | Huston et al. |
| 5,114,711 | A | 5/1992 | Bell et al. |
| 5,116,964 | A | 5/1992 | Capon et al. |
| 5,196,320 | A | 3/1993 | Gillies |
| 5,199,942 | A | 4/1993 | Gillis |
| 5,225,538 | A | 7/1993 | Capon et al. |
| 5,258,498 | A | 11/1993 | Huston et al. |
| 5,314,995 | A | 5/1994 | Fell, Jr. et al. |
| 5,359,035 | A | 10/1994 | Habermann |
| 5,399,346 | A | 3/1995 | Anderson et al. |
| 5,428,130 | A | 6/1995 | Capon et al. |
| 5,457,038 | A | 10/1995 | Trinchieri et al. |
| 5,514,582 | A | 5/1996 | Capon et al. |
| 5,541,087 | A | 7/1996 | Lo et al. |
| 5,585,097 | A | 12/1996 | Bolt et al. |
| 5,601,819 | A | 2/1997 | Wong et al. |
| 5,645,835 | A | 7/1997 | Fell, Jr. et al. |
| 5,650,150 | A | 7/1997 | Gillies |
| 5,650,492 | A | 7/1997 | Gately et al. |
| 5,677,425 | A | 10/1997 | Bodmer et al. |
| 5,679,543 | A | 10/1997 | Lawlis |
| 5,723,125 | A | 3/1998 | Chang et al. |
| 5,726,044 | A | 3/1998 | Lo et al. |
| 5,770,195 | A | 6/1998 | Hudziak et al. |
| 5,827,516 | A | 10/1998 | Urban et al. |
| 5,827,703 | A | 10/1998 | Debs et al. |
| 5,843,423 | A | 12/1998 | Lyman et al. |
| 5,858,347 | A | 1/1999 | Bauer et al. |
| 5,891,680 | A | 4/1999 | Lieschke et al. |
| 5,908,626 | A | 6/1999 | Chang et al. |
| 5,922,685 | A | 7/1999 | Rakhmilevich et al. |
| 5,994,104 | A | 11/1999 | Anderson et al. |
| 6,100,387 | A | 8/2000 | Herrmann et al. |
| 6,309,636 | B1 | 10/2001 | do Couto et al. |
| 6,335,176 | B1 | 1/2002 | Inglese et al. |
| 6,475,717 | B1 | 11/2002 | Enssle et al. |
| 6,617,135 | B1 | 9/2003 | Gillies et al. |

(Continued)

FOREIGN PATENT DOCUMENTS

| | | |
|---|---|---|
| AU | 21725/88 | 3/1989 |
| EP | 0294703 | 12/1988 |
| EP | 0308936 | 3/1989 |
| EP | 0314317 | 5/1989 |
| EP | 0318554 | 6/1989 |
| EP | 0326120 | 8/1989 |
| EP | 0428596 | 5/1991 |
| EP | 0433827 | 6/1991 |
| EP | 0439095 | 7/1991 |
| EP | 0511747 | 11/1992 |
| EP | 0601043 | 6/1994 |

(Continued)

OTHER PUBLICATIONS

Belladonna et al, 2013. Biotechnology and Genetic Engineering Reviews. 29(2): 149-174.*

(Continued)

*Primary Examiner* — Zachary Howard

(74) *Attorney, Agent, or Firm* — Goodwin Procter LLP

(57) ABSTRACT

Modified interleukin-12 (IL-12) p40 polypeptides are disclosed. The modified polypeptides have alterations in the IL-12p40 subunit to eliminate the protease site between positions Lys260 and Arg261. The modified IL-12p40 polypeptides according to the invention have improved stability compared to wild-type mature human IL-12p40 polypeptides.

26 Claims, 17 Drawing Sheets

(56) References Cited

U.S. PATENT DOCUMENTS

| | | | |
|---|---|---|---|
| 6,627,615 | B1 | 9/2003 | Debs et al. |
| 6,646,113 | B1 | 11/2003 | Dreyfuss et al. |
| 6,838,260 | B2 | 1/2005 | Gillies et al. |
| 6,838,360 | B2 | 1/2005 | Kumazaki |
| 6,969,517 | B2 | 11/2005 | Gillies et al. |
| 6,992,174 | B2 | 1/2006 | Gillies et al. |
| 7,067,110 | B1 | 6/2006 | Gillies et al. |
| 7,091,321 | B2 | 8/2006 | Gillies et al. |
| 7,141,651 | B2 | 11/2006 | Gillies et al. |
| 7,148,321 | B2 | 12/2006 | Gillies et al. |
| 7,169,904 | B2 | 1/2007 | Gillies et al. |
| 7,186,804 | B2 | 3/2007 | Gillies et al. |
| 7,872,107 | B2 | 1/2011 | Webster et al. |
| 8,188,248 | B2 | 5/2012 | Webster et al. |
| 2002/0034765 | A1 | 3/2002 | Daugherty et al. |
| 2002/0037558 | A1 | 3/2002 | Lo et al. |
| 2002/0081664 | A1 | 6/2002 | Lo et al. |
| 2002/0146388 | A1 | 10/2002 | Gillies |
| 2002/0147311 | A1 | 10/2002 | Gillies et al. |
| 2002/0193570 | A1 | 12/2002 | Gillies et al. |
| 2003/0044423 | A1 | 3/2003 | Gillies et al. |
| 2003/0049227 | A1 | 3/2003 | Gillies et al. |
| 2003/0105294 | A1 | 6/2003 | Gillies et al. |
| 2003/0133939 | A1 | 7/2003 | Ledbetter et al. |
| 2003/0139365 | A1 | 7/2003 | Lo et al. |
| 2003/0139575 | A1 | 7/2003 | Gillies |
| 2003/0153043 | A1 | 8/2003 | Carr et al. |
| 2003/0157054 | A1 | 8/2003 | Gillies et al. |
| 2003/0166163 | A1 | 9/2003 | Gillies |
| 2003/0166877 | A1 | 9/2003 | Gillies et al. |
| 2004/0033210 | A1 | 2/2004 | Gillies |
| 2004/0043457 | A1 | 3/2004 | Schumacher et al. |
| 2004/0053366 | A1 | 3/2004 | Lo et al. |
| 2004/0072299 | A1 | 4/2004 | Gillies et al. |
| 2004/0082039 | A1 | 4/2004 | Gillies et al. |
| 2004/0180035 | A1 | 9/2004 | Gillies |
| 2004/0180386 | A1 | 9/2004 | Carr et al. |
| 2004/0203100 | A1 | 10/2004 | Gillies et al. |
| 2005/0042729 | A1 | 2/2005 | Lo et al. |
| 2005/0069521 | A1 | 3/2005 | Gillies et al. |
| 2005/0137384 | A1 | 6/2005 | Gillies et al. |
| 2005/0164352 | A1 | 7/2005 | Lauder et al. |
| 2005/0192211 | A1 | 9/2005 | Gillies et al. |
| 2005/0202021 | A1 | 9/2005 | Gillies |
| 2005/0202538 | A1 | 9/2005 | Gillies et al. |
| 2005/0244418 | A1 | 11/2005 | Gillies et al. |
| 2005/0261229 | A1 | 11/2005 | Gillies et al. |
| 2006/0025573 | A1 | 2/2006 | Gillies et al. |
| 2006/0034836 | A1 | 2/2006 | Gillies et al. |
| 2006/0141581 | A1 | 6/2006 | Gillies et al. |
| 2006/0194952 | A1 | 8/2006 | Gillies et al. |
| 2006/0228332 | A1 | 10/2006 | Gillies et al. |
| 2006/0263856 | A1 | 11/2006 | Gillies et al. |
| 2007/0036752 | A1 | 2/2007 | Gillies et al. |

FOREIGN PATENT DOCUMENTS

| | | |
|---|---|---|
| EP | 0659439 | 6/1995 |
| EP | 0790309 | 8/1997 |
| EP | 1088888 | 4/2001 |
| EP | 1176195 | 1/2002 |
| WO | WO-88/07089 | 9/1988 |
| WO | WO-88/09344 | 12/1988 |
| WO | WO-89/09620 | 10/1989 |
| WO | WO-91/04329 | 4/1991 |
| WO | WO-91/08298 | 6/1991 |
| WO | WO-91/13166 | 9/1991 |
| WO | WO-92/02240 | 2/1992 |
| WO | WO-92/08495 | 5/1992 |
| WO | WO-92/08801 | 5/1992 |
| WO | WO-92/10755 | 6/1992 |
| WO | WO-92/16562 | 10/1992 |
| WO | WO-93/03157 | 2/1993 |
| WO | WO-94/25609 | 11/1994 |
| WO | WO-95/05468 | 2/1995 |
| WO | WO-96/08570 | 3/1996 |
| WO | WO-97/00317 | 1/1997 |
| WO | WO-97/20062 | 6/1997 |
| WO | WO-97/24137 | 7/1997 |
| WO | WO-97/30089 | 8/1997 |
| WO | WO-98/52976 | 11/1998 |
| WO | WO-99/03887 | 1/1999 |
| WO | WO-99/29732 | 6/1999 |
| WO | WO-00/34317 | 6/2000 |
| WO | WO-01/18051 | 3/2001 |
| WO | WO-01/40257 | 6/2001 |
| WO | WO-02/056910 | 7/2002 |
| WO | WO-02/069232 | 9/2002 |
| WO | WO-02/079232 | 10/2002 |

OTHER PUBLICATIONS

Afonso et al., (1994), "The Adjuvant Effect of Interleukin-12 in a Vaccine Against Leishmania Major," Science, 263:235-237.

Barbulescu et al., (1998), "IL-12 and IL-18 Differentially Regulate the Transcriptional Activity of the Human IFN-γ Promoter in Primary CD4+ T Lymphocytes," J. Immunol., 160:3642-47.

Batova et al., (1999), "The Ch14.18-GM-CSF Fusion Protein is Effective at Mediating Antibody-Dependent Cellular Cytotoxicity and Complement-Dependent Cytotoxicity in Vitro," Clinical Cancer Research, 5:4259-4263.

Becker et al., (1996), "An Antibody-Interleukin 2 Fusion Protein Overcomes Tumor Heterogeneity by Induction of a Cellular Immune Response," Proc. Natl. Acad. Sci. USA, 93:7826-7831.

Becker et al., (1996), "Eradication of Human Hepatic and Pulmonary Melanoma Metastases in SCID Mice by Antibody-Interleukin 2 Fusion Proteins," Proc. Natl. Acad. Sci. USA, 93:2702-2707.

Becker et al., (1996), "Long-lived and Transferable Tumor Immunity in Mice after Targeted Interleukin-2 Therapy," J. Clin. Invest., 98(12):2801-2804.

Becker et al., (1996), "T Cell-Mediated Eradication of Murine Metastatic Melanoma Induced by Targeted Interleukin-2 Therapy," J. Exp. Med., 183(50):2361-2366.

Beutler et al., (1988), "Tumor Necrosis, Cachexia, Shock, and Inflammation: A Common Mediator," Annual Rev. Biochem., 57:505-518.

Bitonti et al. (2004), "Pulmonary Delivery of an Erythropoietin Fc Fusion Protein in Non-Human Primates Through an Immunoglobulin Transport Pathway," Proc. Natl. Acad. Sci. USA, 101(26):9763-9768.

Bjorn et al., (1985), "Evaluation of Monoclonal Antibodies for the Development of Breast Cancer Immunotoxins," Cancer Research, 45:1214-1221.

Boulianne et al., (1984), "Production of Functional Chimaeric Mouse/Human Antibody," Nature, 312:643-6.

Bubenik et al., (1995), "Interleukin-2 Gene Therapy of Residual EL-4 Leukaemia Potentiates the Effect of Cyclophosphamide Pretreatment," J. Cancer Res. Clin. Oncol., 121:39-43.

Burgess et al., (1990), "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue,"Journal of Cell Biology, 111:2129-2138.

Capon et al., (1989), "Designing CD4 Immunoadhesins for AIDS Therapy," Nature, 337:525-531.

Caton et al., (1986), "Structural and Functional Implications of a Restricted Antibody Response to a Defined Antigenic Region on the Influenza Virus Hemagglutinin," The EMBO Journal, 5(7):1577-1587.

Chamow et al., (1996), "Immunoadhesins: Principles and Applications," Trends in Biotechnology, 14(2):52-60.

Chan et al., (1991), "Induction of Interferon-γ Production by Natural Killer Cell Stimulatory Factor: Characterization of the Responder Cells and Synergy with Other Inducers," J. Exp. Med., 173: 869-879.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," J. Immunol., 148:92-98.

(56) References Cited

OTHER PUBLICATIONS

Chaudhary et al., (1988), "Selective Killing of HIV-Infected Cells by Recombinant Human CD4-Pseudomonas Exotoxin Hybrid Protein," Nature, 335:370-372.
Chaudhary et al., (1989), "A Recombinant Immunotoxin Consisting of Two Antibody Variable Domains Fused to Pseudomonas Exotoxin," Nature, 339:394-397.
Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," J. Immunol., 159(1):351-358.
Cheon et al., (1994), "High-affinity Binding Sites for Related Fibroblast Growth Factor Ligands Reside within Different Receptor Immunoglobulin-Like Domains," Proc. Natl. Acad. Sci. USA, 91: 989-993.
Cohen et al., (1998), "An Artificial Cell-Cycle Inhibitor Isolated from a Combinatorial Library," Proc. Natl. Acad. Sci. USA, 95:14272-7.
Colman et al. (1994), "Effects of Amino Acid Sequence Changes on Antibody-Antigen Interactions," Res. Immunol., 145:33-36.
Colombo et al., (1996), "Amount of Interleukin 12 Available at the Tumor Site is Critical for Tumor Regression," Cancer Research, 56:2531-2534.
Connor et al., (2004), "Ex vivo Evaluation of Anti-EpCAM Immunocytokine huKS-IL2 in Ovarian Cancer," J. Immunotherapy, 27:211-219.
Couto et al., (1994) "Humanization of KC4G3, an Anti-Human Carcinoma Antibody," Hybridoma, 3:215-219.
Cruse et al., (eds.), (1995), Illustrated Dictionary of Immunology, pp. 156-158, CRC Press, NY.
D'Andrea et al., (1992), "Production of Natural Killer Cell Stimulatory Factor (Interleukin 12) by Peripheral Blood Mononuclear Cells," J. Exp. Med., 176:1387-1398.
Database JPO Proteins Sequence Accession No. BD507325 "Process for Producing Highly Pure Protein, Interleukin-12, Protein Inhibiting Interleukin-12 Activity, Remedies for Mammalian Immunopathy and Method of Treating lmmunopathy," Aug. 27, 2002.
Database UniProt EBI Accession No. Q865W9 "Interleukin-12 Subunit Beta Precursor (IL-12B) (IL-12 Subunit p40) (Cytotoxic Lymphocyte Maturation Factor 40kDa Subunit) (CLMF p40)," Jun. 1, 2003.
Database Uniprot, (Jul. 21, 1986), Database Accession No. P01859.
Davis et al., (2003), "Immunocytokines: Amplification of Anti-cancer Immunity," Cancer Immunol. Immunother., 52:297-308.
Desai et al., (1992), "IL-12 Receptor. II. Distribution and Regulation of Receptor Expression," J. Immunol., 148:3125-32.
Dolman et al., (1998), "Suppression of Human Prostate Carcinoma Metastases in Severe Combined Immunodeficient Mice by Interleukin 2 Immunocytokine Therapy," Clin. Cancer Research. , 4(10):2551-2557.
Fell et al., (1991), "Genetic Construction and Characterization of a Fusion Protein Consisting of a Chimeric F(ab') with Specificity for Carcinomas and Human IL-2," J. Immunology, 146(7):2446-2452.
Fell et al., (1992), "Chimeric L6 Anti-Tumor Antibody: Genomic Construction, Expression, and Characterization of the Antigen Binding Site," J. Biological Chemistry, 267:15552-15558.
Frost et al., (1997), "A Phase I/IB Trial of Murine Monoclonal Anti-GD2 Antibody 14.G2a Plus Interleukin-2 in Children with Refractory Neuroblastoma," Cancer, 80(2):317-333.
Gan et al., (1999), "Specific Enzyme-linked Immunosorbent Assays for Quantitation of Antibody-Cytokine Fusion Proteins," Clinical and Diagnostic Laboratory Immunology, 6(2):236-42.
Gasson et al., (1984), "Purified Human Granulocyte Macrophage Colony-Stimulating Factor: Direct Action on Neutrophils," Science, 226:1339-1342.
Gately et al., (1998), "The Interleukin-12/Interleukin-12-Receptor System: Role in Normal and Pathologic Immune Responses," Annu. Rev. Immunol., 16:495-521.
Gearing et al., (1991), "Homology of the p40 Subunit of Natural Killer Cell Stimulatory Factor (NKSF) with the Extracellular Domain of the Interleukin-6 Receptor," Cell, 66:9-10.
Gillessen et al., (1995), "Mouse Interleukin-12 (IL-12) p40 Homodimer: A Potent IL-12 Antagonist," Eur. J. Immunol., 25:200-206.
Gillies et al., (1989), "Expression of Human Anti-Tetanus Toxoid Antibody in Transfected Murine Myeloma Cells," Bio/Technology, 7:799-804.
Gillies et al., (1989), "High-Level Expression of Chimeric Antibodies Using Adapted cDNA Variable Region Cassettes," J. Immunol. Methods, 125:191-202.
Gillies et al., (1990), "Antigen Binding and Biological Activities of Engineered Mutant Chimeric Antibodies with Human Tumor Specificities," Hum. Antibod. Hybridomas, 1(1):47-54.
Gillies et al., (1991), "Expression of Genetically Engineered Immunoconjugates of Lymphotoxin and a Chimeric Anti-Ganglioside GD2 Antibody," Hybridoma., 10(3):347-56.
Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/ Recombinant Antibody," J. Immunology, 146(3):1067-1071.
Gillies et al., (1992), "Antibody-Targeted Interleukin 2 Stimulates T-Cell Killing of Autologous Tumor Cells," Proc. Natl. Acad. Sci. USA, 89:1428-1432.
Gillies et al., (1993), "Biological Activity and In Vivo Clearance of Antitumor Antibody/Cytokine Fusion Proteins," Bioconjugate Chem., 4(3):230-235.
Gillies et al., (1998), "Antibody-IL-12 Fusion Proteins are Effective in SCID Mouse Models of Prostate and Colon Carcinoma Metastases," J. Immunology, 160:6195-6203.
Gillies et al., (1999), "Improving the Efficacy of Antibody-Interleukin 2 Fusion Proteins by Reducing Their Interaction with Fc Receptors," Cancer Research, 59:2159-2166.
Gillies et al., (2002), "Bi-Functional Cytokine Fusion Proteins for Gene Therapy and Antibody-targeted Treatment of Cancer," Cancer Immunol. Immunother., 51(8):449-60.
Gillies et al., (2002), "Improved Circulating Half-life and Efficacy of an Antibody-interleukin 2 Immunocytokine Based on Reduced Intracellular Proteolysis," Clin. Cancer Research, 8(1):210-216.
Goeddel et al., (1986), "Tumor Necrosis Factors: Gene Structure and Biological Activities," Cold Spring Harb. Symp. Quant. Biol., 51:597-609.
Gren et al., (1983), "A New Type of Leukocytic Interferon," English Translation of Dokl. Akad. Nauk. SSSR., 269(4):986-990.
Grimaldi et al., (1989), "The t(5;14) Chromosomal Translocation in a Case of Acute Lymphocytic Leukemia Joins the Interleukin-3 Gene to the Immunoglobulin Heavy Chain Gene," Blood, 73(8):2081-2085.
Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," J. Clin. Invest., 82:1956-1962.
Guyre et al., (1997), "Increased Potency of Fc-Receptor-Targeted Antigens," Cancer Immunol. Immunother., 45:146-148.
Halin et al., (2002), "Enhancement of the Antitumor Activity of Interleukin-12 by Targeted Delivery to Neovasculature," Nature Biotechnology, 20:264-269.
Hank et al., (1996), "Activation of Human Effector Cells by a Tumor Reactive Recombinant Anti-ganglioside GD2 Interleukin-2 Fusion Protein (ch14.18-IL2)," Clin Cancer Research, 2(12):1951-1959.
Hank et al., (2003), "Determination of Peak Serum Levels and Immune Response to the Humanized Anti-Ganglioside Antibody-Interleukin-2 Immunocytokine," in Methods in Molecular Medicine, 85: Novel Anticancer Drug Protocols, Buolamwini et al., (eds.), pp. 123-131, Humana Press Inc., Totowana, NJ.
Harris et al., (1993), "Therapeutic Antibodies—the Coming of Age," Trends in Biotechnology, 11:42-44.
Harris, (1995), "Processing of C-terminal Lysine and Arginine Residues of Proteins Isolated from Mammalian Cell Culture," J. Chromatography A, 705:129-134.
Harvill et al., (1995), "An IgG3-IL2 Fusion Protein Activates Complement, Binds FcγRI, Generates LAK Activity and Shows Enhanced Binding to the High Affinity IL-2R," Immunotechnology, 1:95-105.

(56) References Cited

OTHER PUBLICATIONS

Harvill et al., (1996), "In Vivo Properties of an IgG3-IL-2 Fusion Protein: a General Strategy for Immune Potentiation," J. Immunology, 157(7):3165-3170.
Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," J. Immunol., 163:583-9.
He et al., (1998), "Humanization and Pharmacokinetics of a Monoclonal Antibody with Specificity for Both E- and P-Selectin," J. Immunology, 160:1029-1035.
Heinzel et al., (1997), "In Vivo Production and Function of IL-12 p40 Homodimers," J. Immunology,158:4381-4388.
Henkart, (1985), "Mechanism of Lymphocyte-Mediated Cytotoxicity," Ann. Rev. Immunol., 3:31-58.
Herrmann et al., (1989), "Hematopoietic Responses With Advanced Malignancy Treated With Recombinant Human Granulocyte-Macrophage Colony-Stimulating Factor," Journal of Clinical Oncology, 7(2):159-167.
Hezareh et al., (2001), "Effector Function Activities of a Panel of Mutants of a Broadly Neutralizing Antibody against Human Immunodeficiency Virus Type 1," J. Virology, 75(24):12161-12168.
Holden et al., (2001), "Augmentation of Antitumor Activity of an Antibody-Interleukin 2 Immunocytokine with Chemotherapeutic Agents," Clinical Cancer Research, 7:2862-2869.
Holden et al., (2001), "Augmentation of Anti-Tumor Activity of KS-IL2 Immunocytokine with Chemotherapeutic Agents," Proceedings of the American Association for Cancer Research, 42:683, Abstract No. 3675 (XP-002195344).
Hornick et al., (1999), "Pretreatment with a Monoclonal Antibody/Interleukin-2 Fusion Protein Directed Against DNA Enhances the Delivery of Therapeutic Molecules to Solid Tumors," Clin. Cancer Research, 5:51-60.
Hurn et al., (1980), "Production of Reagent Antibodies," Methods in Enzymology, 70:104-142.
Imboden et al., (2001), "The Level of MHC Class I Expression on Murine Adenocarcinoma Can Change the Antitumor Effector Mechanism of Immunocytokine Therapy," Cancer Research, 61(4):1500-7.
International Search Report for PCT/EP2006/012301, mailed Jun. 15, 2007 (6 pages).
Jefferis et al., (1998), "IgG-Fc-Mediated Effector Functions: Molecular Definition of Interaction Sites for Effector Ligands and the Role of Glycosylation," Immunological Reviews, 163:59-76.
Jung et al., (1986), "Activation of Human Peripheral Blood Mononuclear Cells by Anti-T3: Killing of Tumor Target Cells Coated with Anti-Target-Anti-T3 Conjugates," Proc. Natl. Acad. Sci. USA, 83:4479-4483.
Kappel et al., (1992), "Regulating Gene Expression in Transgenic Animals," Current Opinion in Biotechnology, 3:548-553.
Kendra et al., (1999), "Pharmacokinetics and Stability of the ch14.18-Interleukin-2 Fusion Protein in Mice," Cancer Immunol. Immunother., 48:219-229.
Kim et al., (1997), "An Ovalbumin-IL-12 Fusion Protein is More Effective than Ovalbumin Plus Free Recombinant IL-12 in Inducing a T Helper Cell Type 1-Dominated Immune Response and Inhibiting Antigen-Specific IgE Production," J. Immunology,158(9):4137-4144.
Kim et al., (1999), "Cytokine Molecular Adjuvants Modulate Immune Responses Induced by DNA Vaccine Constructs for HIV-1 and SIV," Journal of Interferon and Cytokine Research, 19:77-84.
Kranz et al., (1984), "Attachment of an Anti-Receptor Antibody to Non-Target Cells Renders Them Susceptible to Lysis by a Clone of Cytotoxic T Lymphocytes," Proc. Natl. Acad. Sci. USA, 81:7922-7926.
Kushner et al., (2001), "Phase II Trial of the Anti-GD2 Monoclonal Antibody 3F8 and Granulocyte-Macrophage Colony-Stimulating Factor for Neuroblastoma," J. Clinical Oncology, 19(22):4189-94.
Lazar et al., (1988), "Transforming Growth Factor α: Mutation of Aspartic Acid 47 and Leucine 48 Results in Different Biological Activities," Molecular and Cellular Biology, 8(3):1247-1252.
Lieschke, et al., (1997), "Bioactive Murine and Human Interleukin-12 Fusion Proteins which Retain Antitumor Activity In Vivo," Nature Biotechnology, 15(1):35-40.
Liu et al., (1985), "Heteroantibody Duplexes Target Cells for Lysis by Cytotoxic T Lymphocytes," Proc. Natl. Acad. Sci. USA, 82:8648-8652.
Lo et al., (1998), "High Level Expression and Secretion of Fc-X Fusion Proteins in Mammalian Cells," Protein Engineering, 11(6):495-500.
Lode et al., (1998), "Gene Therapy with a Single Chain Interleukin 12 Fusion Protein Induces T Cell-Dependent Protective Immunity in a Syngeneic Model of Murine Neuroblastoma," Proc. Natl. Acad. Sci. USA, 95:2475-80.
Lotze et al., (1996), "Cytokine Gene Therapy of Cancer Using Interleukin-12: Murine and Clinical Trials," Ann. NY Acad. Sci., 795:440-54.
Lund et al., (1993), "Control of IgG/Fc Glycosylation: A Comparison of Oligosaccharides from Chimeric Human/Mouse and Mouse Subclass Immunoglobulin Gs," Mol. Immunol., 30(8):741-748.
MacLean et al., (1996), "Enhancing the Effect of Theratope STn-KLH Cancer Vaccine in Patients with Metastatic Breast Cancer by Pretreatment with Low-Dose Intravenous Cyclophosphamide," J. Immunother., 19(4):309-316.
Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," FASEBJ., 11:765-74.
Martinotti et al., (1995), "CD4 T Cells Inhibit in vivo the CD8-Mediated Immune Response Against Murine Colon Carcinoma Cells Transduced with Interleukin-12 Genes," Eur. J. Immunol. 25:137-146.
Mateo et al., (2000), "Removal of Amphipathic Epitopes from Genetically Engineered Antibodies: Production of Modified Immunoglobulins with Reduced Immunogenicity," Hybridoma, 19(6):463-471.
McMahan et al., (1991), "A Novel IL-1 Receptor, Cloned From B-Cells by Mammalian Expression is Expressed in Many Cell Types," EMBO J., 10:2821-32.
Mehrotra et al., (1993), "Effects of IL-12 on the Generation of Cytotoxic Activity in Human CD8+ T Lymphocytes," J. Immunol., 151:2444-52.
Michaelsen et al., (1977), "Primary Structure of the Hinge Region of Human IgG3," J. Biol. Chem., 252(3):883-889.
Miyake et al., (1988), "Synthesis of Recombinant Human Single-Chain Urokinase-Type Plasminogen Activator Variants Resistant to Plasmin and Thrombin," J. Biochem., 104:643-647.
Mosmann et al., (1989), "TH1 and TH2 Cells: Different Patterns of Lymphokine Secretion Lead to Different Functional Properties," Ann. Rev. Immunol., 7:145-173.
Mueller et al., (1990), "Enhancement of Antibody-Dependent Cytotoxicity With A Chimeric Anti-GD2 Antibody," J. Immunology, 144(4):1382-1386.
Mueller et al., (1990), "Serum Half-Life and Tumor Localization of a Chimeric Antibody Deleted of the CH2 Domain and Directed Against the Disialoganglioside GD2," Proc. Natl. Acad. Sci. USA., 87:5702-5705.
Mueller et al., (1997), "Humanized Porcine VCAM-specific Monoclonal Antibodies with Chimeric IgG2/G4 Constant Regions Block Human Leukocyte Binding to Porcine Endothelial Cells," Molecular Immunology, 34(6):441-452.
Mullins et al., (1998), "Interleukin-12 Overcomes Paclitaxel-Mediated Suppression of T-Cell Proliferation," Immunopharmacol. Immunotoxicol., 20(4):473-492.
Murphy et al., (1986), "Genetic Construction, Expression, and Melanoma-Selective Cytotoxicity of a Diphtheria Toxin-Related α-Melanocyte-Stimulating Hormone Fusion Protein," Proc. Natl. Acad. Sci. USA, 83:8258-8262.

(56) References Cited

OTHER PUBLICATIONS

Murphy, (1988), "Diphtheria-Related Peptide Hormone Gene Fusions: A Molecular Gene Approach to Chimeric Toxin Development," in Immunotoxins, pp. 123-140, Frankel (ed.), Kluwer Acad. Pub.
Naramura et al., (1993), "Therapeutic Potential of Chimeric and Murine Anti-(Epidermal Growth Factor Receptor) Antibodies in a Metastasis Model for Human Melanoma," Cancer Immuno. Immunother., 37:343-349.
Nastala et al., (1994), "Recombinant IL-12 Administration Induces Tumor Regression in Association with IFN-γ Production," J. Immunol., 153:1697-706.
Neal et al., (2003), "NXS2 Murine Neuroblastomas Express Increased Levels of MHC Class I Antigens upon Recurrence Following NK-dependent Immunotherapy," Cancer Immunol. Immunother., 53:41-52.
Neal et al., (2004), "Enhanced Activity of Hu14.18-IL2 Immunocytokine against Murine NXS2 Neuroblastoma when Combined with Interleukin-2 Therapy," Clin. Cancer. Res., 10:4839-4847.
Nedwin et al., (1985), "Human Lymphotoxin and Tumor Necrosis Factor Genes: Structure, Homology and Chromosomal Localization," Nucleic Acids Research, 13(17):6361-6373.
Nelles et al., (1987), "Characterization of Recombinant Human Single Chain Urokinase-Type Plaminogen Activtor Mutants Produced by Site-Specific Mutagenesis of Lysine 158," J. Biol. Chem., 262(12):5682-5689.
Ngo et al., (1994), "Computational Complexity, Protein Structure Prediction, and the Levinthal Paradox," in The Protein Folding Problem and Tertiary Structure Prediction, Merz et al. (eds.), pp. 433-440 and 492-495, Birkhauser, Boston, MA.
Odbileg et al., (2004), "Cloning and Sequence Analysis of Llama Cytokines Related to Cell-Mediated Immunity," Vet. Immunol. Immunopathol., 102:93-102.
Padlan et al., (1991), "A Possible Procedure for Reducing the Immunogenicity of Antibody Variable Domains while Preserving Their Ligand Binding Properties," Mol. Immunol., 28:489-498.
Palucka et al., (1998), "Dendritic Cells as the Terminal Stage of Monocyte Differentiation," J. Immunol., 160:4587-95.
Pastan et al., (1989), "Pseudomonas Exotoxin: Chimeric Toxins," Journal of Biological Chemistry, 264(26):15157-15160.
Paul et al., (1988), "Lymphotoxin," Ann. Rev. Immunol., 6.407-438.
Perussia et al., (1992), "Natural Killer (NK) Cell Stimulatory Factor or IL-12 Has Differential Effects on the Proliferation of TCR-αβ+, TCR-γδ+ T Lymphocytes, and NK Cells," J. Immunol., 149:3495-502.
Putzer et al., (1997), "Interleukin 12 and B7-1 Costimulatory Molecule Expressed by an Adenovirus Vector Act Synergistically to Facilitate Tumor Regression," Proc. Natl. Acad. Sci. USA, 94(20):10889-10894.
Ravetch, (1997), "Fc Receptors," Curr. Opin. Immunol., 9:121-125.
Robinson et al., (1998), "Optimizing the Stability of Single-Chain Proteins by Linker Length and Composition Mutagenesis," Proc. Natl. Acad. Sci. USA, 95:5929-34.
Schlom (1991), "Monoclonal Antibodies: They're More and Less Than You Think," in Molecular Foundations of Oncology, pp. 95-133.
Schoenhaut et al., (1992), "Cloning and Expression of Murine IL-12," J. Immunology, 148(10:3433-3340.
Sharma et al., (1999), "T cell-Derived IL-10 Promotes Lung Cancer Growth by Suppressing Both T cell and APC Function," Journal of Immunology, 163:5020-5028.
Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity," Nucleic Acids Res., 16(17):8207-8211.
Shen et al., (1986), "Heteroantibody-Mediated Cytotoxicity: Antibody to the High Affinity Fc Receptor for IgG Mediates Cytotoxicity by Human Monocytes that is Enhanced by Interferon-γ and is Not Blocked by Human IgG," J. Immunology,137(11):3378-3382.
Tao et al., (1991), "The Differential Ability of Human IgG1 and IgG4 to Activate Complement Is Determined by the COOH-terminal Sequence of the $C_{H2}$ Domain," J. Exp. Med., 173:1025-1028.
The Merck Manual of Diagnosis and Therapy, 17th Ed., (1999) pp. 990-993 and 1278-1283.
Thurner, (1999), "Generation of Large Numbers of Fully Mature and Stable Dendritic Cells from Leukapheresis Products for Clinical Application," J. Immunol. Methods, 223:1-15.
Tiruppathi et al., (1996), "Isolation and Characterization of a Cell Surface Albumin-Binding Protein from Vascular Endothelial Cells," Proc. Nat. Acad. Sci. USA, 93:250-4.
Trinchieri et al., (1992), "Natural Killer Cell Stimulatory Factor (NKSF) or Interleukin-12 is a Key Regulator of Immune Response and Inflammation," Progress in Growth Factor Research, 4:355-368.
Trinchieri, (1994), "Interleukin-12: A Cytokine Produced by Antigen-Presenting Cells With Immunoregulatory Functions in the Generation of T-Helper Cells Type 1 and Cytotoxic Lymphocytes," Blood, 84:4008-4027.
Vagliani et al., (1996), "Interleukin 12 Potentiates the Curative Effect of a Vaccine Based on Interleukin 2-transduced Tumor Cells," Cancer Research, 56:467-470.
Vitetta et al., (1987), "Redesigning Nature's Poisons to Create Anti-Tumor Reagents," Science, 238:1098-1104.
Voest et al., (1995), "Inhibition of Angiogenesis in Vivo by Interleukin 12," J. Natl. Canc. Inst., 87:581-6.
Weber et al., (2001), "Phase I Trial of huKS-IL2 Immunocytokine in Patients with Prostate Carcinoma: Clinical, PK, and Biological PD Results (Abstract)," American Society of Clinical Oncology Program/Proceedings, 20(Part 1):259a.
Weitkamp et al., (1973), "Additional Data on the Population Distribution of Human Serum Albumin Genes; Three New Variants," Ann. Hum. Genet., 37:219-26.
Wells, (1990), "Additivity of Mutational Effect in Proteins," Biochemistry, 29(37):8509-8517.
Wolf et al., (1991), "Cloning of cDNA for Natural Killer Cell Stimulatory Factor, A Heterodimeric Cytokine with Multiple Biologic Effects on T and Natural Killer Cells," J. Immunol., 146:3075-3081.
Written Opinion of the International Searching Authority for PCT/EP2006/012301, mailed Jun. 15, 2007 (4 pages).
Wysocka et al., (1995), "Interleukin-12 is Required for Interferon-γ Production and Lethality in Lipopolysaccharide-Induced Shock in Mice," Eur. J. Immunol., 25:672-6.
Yeh et al., (1992), "Design of Yeast-Secreted Albumin Derivatives for Human Therapy: Biological and Antiviral Properties of a Serum Albumin-CD4 Genetic Conjugate," Proc. Natl. Acad. Sci. USA, 89:1904-8.
Yokota et al., (1986), "Isolation and Characterization of a Human Interleukin cDNA Clone, Homologous to Mouse B-Cell Stimulatory Factor 1, that Expresses B-Cell- and T-Cell-Stimulating Activities," Proc. Natl. Acad. Sci. USA, 83:5894-5898.
Yoon et al., (2000), "Charged Residues Dominate a Unique Interlocking Topography in the Heterodimeric Cytokine Interleukin-12," EMBO Journal, 19:3530-3541.
Zagozdzon et al., (1999), "Potentiation of Antitumor Effects of IL-12 in Combination with Paclitaxel in Murine Melanoma Model In Vivo," International Journal of Molecular Medicine, 4:645-648.
Altschul et al., (1990), "Basic local alignment search tool," J. Mol. Biol., 215:403-10.
Altschul et al., (1997), "Gapped BLAST and PSI-BLAST: A New Generation of Protein Database Search Programs," Nucleic Acids Res., 25:3389-3402.
Atkins et al., (1997), "Phase I Evaluation of Intravenous Recombinant Human Interleukin 12 in Patients with Advanced Malignancies," Clin. Cancer Res., 3:409-17.
Brunda et al., (1993), "Antitumor and Antimetastatic Activity of Interleukin 12 Against Murine Tumors," J. Exp. Med., 178:1223-30.
Colombo and Trinchieri, (2002), "Interleukin-12 in Anti-Tumor Immunity and Immunotherapy," Cytokine & Growth Facter Rev., 13:155-168.
Gately et al., (1995), "Measurement of Human and Mouse Interleukin-12," Curr Protoc Immunol., Unit 6.16.

(56) References Cited

OTHER PUBLICATIONS

Gollob et al., (2000), "Phase I Trial of Twice-Weekly Intravenous Interleukin 12 in Patients with Metastatic Renal Cell Cancer or Malignant Melanoma: Ability to Maintain IFN-gamma Induction is Associated with Clinical Response," Clin. Cancer Res.,6:1678-92.
Hikawa et al., (2004), "Interleukin-12 p40-Homodimer Production in Sensory Dorsal Root Ganglion Neurons," Neuroscience, 129:75-83.
Hunter CA., (2005), "New IL-12-Family Members: IL-23 and IL-27, Cytokines with Divergent Functions," Nat Rev Immunol., 5:521-531.
Hurteau et al., (2001), "Evaluation of Recombinant Human Interleukin-12 in Patients with Recurrent or Refractory Ovarian cancer: a Gynecologic Oncology Group Study," Gynecol. Oncol, 82:7-10.
Karlin and Altschul, (1990), "Methods for Assessing the Statistical Significance of Molecular Sequence Features by Using General Scoring Schemes," Proc Natl. Acad. Sci. USA, 87:2264-68.
Karlin and Altschul, (1993), "Applications and Statistics for Multiple High-Scoring Segments in Molecular Sequences," Proc Natl. Acad. Sci. USA, 90:5873-77.
Kobayashi et al., (1989), "Identification and Purification of Natural Killer Cell Stimulatory Factor (NKSF), a Cytokine with Multiple Biologic Effects on Human Lymphocytes," J. Exp Med., 170:827-845.
Langrish et al., (2004), "IL-12 and IL-23: Master Regulators of Innate and Adaptive Immunity," Immunol. Rev., 202:96-105.
Lee et al., (2001), "Effects of Interleukin-12 on the Immune Response to a Multipeptide Vaccine for Resected Metastatic Melanoma," J. Clin. Oncol., 19:3836-47.
Leong et al., (2003), "Optimized Expression and Specific Activity of IL-12 by Directed Molecular Evolution," Proc. Natl. Acad. Sci. USA, 100:1163-1168.
Oppmann et al., (2000), "Novel p19 Protein Engages IL-12p40 to Form a Cytokine, IL-23, with Biological Activities Similar As Well As Distinct from IL-12," Immunity, 13:715-725.
Sturniolo et al., (1999), "Generation of Tissue-Specific and Promiscuous HLA Ligand Databases Using DNA Microarrays and Virtual HLA class II Matrices," Nature Biotech., 17:555-61.
Hasan et al., (1999) "IL-12 is a Heparin-Binding Cytokine," Journal of Immunology, 162:1064-70.
Campanella et al., (2003) "CXCR3 and Heparin Binding Sites of the Chemokine IP-10 (CXCL 10)," Journal of Biological Chemistry, 278(19): 17066-74.
Russell et al., (2004) "IL-12 p40 Homodimer-Dependent Macrophage Chemotaxis and Respiratory Viral Inflammation are Mediated Through IL-12 Receptor β1," Journal of Immunology, 171: 6866-74.
Ferrer-Costa et al., (2007) "Characterization of Compensated Mutations in Terms of Structural and Physico-Chemical Properties," J Mol Biol. 365: 249-56.
Wells (1990) "Additivity of Mutational Effects in Proteins," Biochemistry 29(37): 8509-17.
Bork (2000) "Powers and Pitfalls in Sequence Analylsis," Genome Research 10:398-400.
Skolnick et al., (2000) "From Genes to Protein Structure and Function: Novel Applications of Computational Approaches in the Genomic Era," Trends in Biotech, 18(1): 34-39.
Doerks et al., (1998) "Protein Annotation: Detective Work for Function Prediction," Trends in Genetics 14(6): 248-50.
Brenner (1999) "Errors in Genome Annotation," Trends in Genetics 15(4): 132-33.
Stenlund et al., (2002) "Structural Requirements for High-Affinity Heparin Binding: Alanine Scanning Analysis of Charged Residues in the C-Terminal Domain of Human Extracellular Superoxide Dismutase," Biochemistry, 41: 3168-3175.
Lefevre et al., (1997) "Alanine-Stretch Scanning Mutagenesis: a Simple and Efficient Method to Probe Protein Structure," Nucleic Acids Research, 25(2):447-48.
Paine-Saunders et al., (2002) "Heparan Sulfate Proteoglycans Retain Noggin at the Cell Surface," Journal of Biological Chemistry, 277(3): 2089-96.
Phillips (2001) "The challenge of gene therapy and DNA delivery," Journal of Pharmacy and Pharmacology, 53:1169-1174.

* cited by examiner

Figure 1

RNLPVATPDPGMFPCLHHSQNLLRAVSNMLQKARQTLEFYPCTSEEIDHE
DITKDKTSTVEACLPLELTKNESCLNSRETSFITNGSCLASRKTSFMMAL
CLSSIYEDLKMYQVEFKTMNAKLLMDPKRQIFLDQNMLAVIDELMQALNF
NSETVPQKSSLEEPDFYKTKIKLCILLHAFRIRAVTIDRVMSYLNAS
(SEQ ID NO:1)

Figure 2

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDI*IKPDPPKNLQLKPLKNSRQVEVSWEYPDTWSTPHSYFSLT*
*FCVQVQGKSKREKKDRVFTDKTSATVICRKNASISVRAQDRYYSSSWSEW*
*ASVPCS*(SEQ ID NO:2)

Figure 3

AVPGGSSPAWTQCQQLSQKLCTLAWSAHPLVGHMDLREEGDEETTNDVPH
IQCGDGCDPQGLRDNSQFCLQRIHQGLIFYEKLLGSDIFTGEPSLLPDSP
VGQLHASLLGLSQLLQPEGHHWETQQIPSLSPSQPWQRLLLRFKILRSLQ
AFVAVAARVFAHGAATLSP
(SEQ ID NO:3)

REKKDRVFTDKTSATVICRKNASISVRAQDRYYSSSWSEWASVPCS
(SEQ ID NO:4)

Figure 6

KSKREKKDR
(SEQ ID NO:5)

Figure 7.1

```
  1 IWELKKDVYVVELDWYPDAPGEMVVLTCDTPEEDGITWTLDQSSEVLGSGKTLTIQVKEF p40 human
  1 ...........................................G................ p40 baboon
  1 ...........................................G................ p40 rhesus
  1 ...........................................G................ p40 mangabey
  1 ....E..........H............H.....D....SA................... p40 dog
  1 ....E.N........H..................D....S.................... p40 cat
  1 ....E.......................N....E.....SA..N................ p40 horse
  1 ....E.N..........N..........N..........S........T......H.... p40 pig
  1 M...E.N...............T................S.................... p40 cow
  1 ....E.N..I............T................S.................... p40 water buffalo
  1 ....E.N..........N....T................S.................... p40 goat
  1 ....E.N..........N....T................S.................... p40 sheep
  1 ....E.N...............T...R............S..............V..... p40 deer
  1 ....E.......V..S...A..R.......S...D.I..S.KN..AV............. p40 hamster
  1 M..............HT.....T.....N.A........S.RK.DI.............. p40 guinea pig
  1 ....E.......V..S.G....R.......S...D.I..S......V......IV..... p40 cotton rat
  1 M...E.......V..R......T.T.....S...D....S..RRG.I........T.R.. p40 rat
  1 M...E.......V..T......T.N.........D....S..RHG.I........T.... p40 mouse

 61 GDAGQYTCHKGGEVLSHSLLLLHKKEDGIWSTDILKDQKEPKNKTFLRCEAKNYSGRFTC p40 human
 61 .............A...................V.......................... p40 baboon
 61 .............A...................V.......................... p40 rhesus
 61 .............A.......P.....................E.............I.. p40 mangabey
 61 ............K...R....I..............E...S...I..K............ p40 dog
 61 A.................F..I.............RE...S...I..K............ p40 cat
 61 ....W.............H.....................S......K............ p40 horse
 61 ........R...A...Q...........................S..K............ p40 pig
 61 .............A..R.........................A.S..K....D...H... p40 cow
 61 .............A..R.........................A.S..K....D...H... p40 water buffalo
 61 ................R.........................A.S..K....D...H... p40 goat
 61 ................R.........................A.S..K....D...H... p40 sheep
 61 ................R.........................A.S..K....D...H... p40 deer
 61 SN..........KT....R.......N............D.......K...A........ p40 hamster
 61 E...G...........R.Q........E........E..GSNG....K...RS....... p40 guinea pig
 61 S.............T...R....................D.......K...A........ p40 cotton rat
 61 L........R...T....H.......N.....E...N---F......K...P........ p40 rat
 61 L............T....H.......N.....E...N---F......K...P........ p40 mouse

121 WWLTTISTDLTFSVKSSRGSSDPQGVTCGAATLSAERVRGDNKEY-EYSVECQEDSACPA p40 human
121 .....................N........V..............-.............. p40 baboon
121 .....................N........V..............-.............. p40 rhesus
121 ...S.........II......N.......................-.............. p40 mangabey
121 ....A.....K........F..........V........V..RD.KK.T.....G....S p40 dog
121 ....A.....K.T.......................K..V..RD.KK.T.....G..... p40 cat
121 ....A.....K............R..............SV.DR..KK.T.....G..... p40 horse
121 ....A.....K.........T..R.....T....EDLG-----..KK.R.....G..... p40 pig
121 ....A.....K............R.......L....K.SLEHR..NK.T.....G..... p40 cow
121 ....A.....K.........A..R.......S....K.SV.HR..NK.T.....G.T... p40 water buffalo
121 S...A...N.K............R.......S....K.SM.HR..NK.T.....G..... p40 goat
121 S...A...N.K............R.......S....K.SM.HR..NK.T.....G..... p40 sheep
121 ....A.....K............R.......S..T.K.IV.HR..KK.T.....G..... p40 deer
121 ....A.....K.N....SS...SRA......S....K.TV.R.D.QK...A....IT..T p40 hamster
121 ....AFG..VK....G.......S....-----E...S....Q..-K............T p40 guinea pig
121 ....AV....K..L...SS...SRS......S..T.K.TV.QRD.NK...A....IT..T p40 cotton rat
118  S..VHRN...K.NI...SS.PESRA....R.S....K.TLNQRD.EK...A....VT..T p40 rat
118  S..VQRNM..K.NI...SS.P.SRA....M.S....K.TL.QRD.EK...S....VT..T p40 mouse
```

Figure 7.2

```
180 AEESLPIEVMVDAVHKLKYENYTSSFFIRDIIKPDPPKNLQLKPLKNSRQVEVSWEYPDT p40 human
180 ...R.........I....................................A......... p40 baboon
180 ...R.........I.............................................. p40 rhesus
180 ...R.........I.............................................. p40 mangabey
181 .........V...I.......................T...........H.......... p40 dog
181 .........V...I...................................H.......... p40 cat
181 ........IV..............G..................................E. p40 horse
176 .........VLE..............................N......H..I....... p40 pig
181 .....L...V.E..............................R................. p40 cow
181 .....L...V.E................................................ p40 water buffalo
181 .........VME..............................R................. p40 goat
181 .........VME..............................R................. p40 sheep
181 .........V.E..............................R................. p40 deer
181 ...T...GLVME.Q..Y.....STG....................RG.-.M.L......S p40 hamster
176 .........V...I..F.........Y.................SV..Q........... p40 guinea pig
181 ...T....LVME.Q..Y.....STG.....................S.-..........S p40 cotton rat
178 ...T....LV.E.QQQN.....ST.................V......-..........S p40 rat
178 ...T....LALE.RQQN.....ST.................M......-..........S p40 mouse

240 WSTPHSYFSLTFCVQVQG--KSKREKKDR---------VF-TDKTSATVICRKNASISVR p40 human
240 .............I....--.........---------I.-...............F..Q p40 baboon
240 .............I....--.........---------I.-...............F..Q p40 rhesus
240 .............I....--.........---------I.-...............F..Q p40 mangabey
241 ...............A..--.NN......---------LC-V.....K.V.H.D.K.R.Q p40 dog
241 ............G.....--.NN......---------LS-V.....K.V.H.D.K.R.Q p40 cat
241 ............SI....--.N.K.R...---------L.-M.E....T.H.DGQ.R.Q p40 horse
236 ..........M.G.....--.N.....K---------L.-..QI..K.T.H.D.N.R.Q p40 pig
241 ..................--.N.....---------L.-M.Q...K.T.H.D.NVR.Q p40 cow
241 ..................--.N.....---------L.-M.Q...K.T.H.D.NVR.Q p40 water buffalo
241 ..................--.N.....---------L.-..Q...K.T.H.D.N.R.Q p40 goat
241 ..................--.N.....---------L.-A.Q...K.T.H.D.N.R.Q p40 sheep
241 ..................--.N.....---------L.-M.Q...K.T.H.D...R.Q p40 deer
240 ..........K.H...HR-----...R..ES---------Q.-V......IR.S.G.EVR.. p40 hamster
236 ............L..TH.KN.NR....YE-----------L.-........S.H.ISKVE.. p40 guinea pig
240 ..........K.F...YR-----.K...GES----------LLV..P..KIR.S.GGEVR.. p40 cotton rat
237 ..........K.F.RI.R-----.K..TKETEEECNQKGA.LVE....E.Q.-.G.N.C.Q p40 rat
237 ..........K.F.RI.R-----.K..MKETEEGCNQKGA.LVE...TE.Q.-.GGNVC.Q p40 mouse

292 AQDRYYSSSWSEWASVPCS                                      p40 human (SEQ ID NO:2)
292 ...................                                      p40 baboon (SEQ ID NO:27)
292 ...................                                      p40 rhesus (SEQ ID NO:28)
292 ..........N..T.....                                      p40 mangabey (SEQ ID NO:29)
293 .R........D....S..                                       p40 dog (SEQ ID NO:30)
293 .R........N....S..                                       p40 cat (SEQ ID NO:31)
293 .R.............S..                                       p40 horse (SEQ ID NO:32)
288 .R.............S.N                                       p40 pig (SEQ ID NO:33)
291 .R......F.......S..                                      p40 cow (SEQ ID NO:34)
291 .R......F.......S..                                      p40 water buffalo (SEQ ID NO:35)
291 .R......F.......S..                                      p40 goat (SEQ ID NO:36)
291 .R......F.......S..                                      p40 sheep (SEQ ID NO:37)
291 .R....N.F.......S..                                      p40 deer (SEQ ID NO:38)
291 ...H..N....R.V.....                                      p40 hamster (SEQ ID NO:39)
290 .R.............S..EVSVSR                                 p40 guinea pig (SEQ ID NO:40)
291 ...H..N.........S.N                                      p40 cotton rat (SEQ ID NO:41)
296 ......N..C.K.TC...RGRS                                   p40 rat (SEQ ID NO:42)
296 ......N..C.K..C...RVRS                                   p40 mouse (SEQ ID NO:43)
```

<u>Figure 8</u>

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQG<u>KDNTER</u>VFTDKTSATVICRKNASISVRAQDRYYSSSWSEWASV
PCS
(SEQ ID NO:6)

<u>Figure 9</u>

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQG<u>KDNTEGR</u>VFTDKTSATVICRKNASISVRAQDRYYSSSWSEWAS
VPCS
(SEQ ID NO:7)

<u>Figure 10</u>

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQG<u>QDQDEKKDR</u>VFTDKTSATVICRKNASISVRAQDRYYSSSWSEW
ASVPCS
(SEQ ID NO:8)

<u>Figure 11</u>

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQG<u>QDQDESGDR</u>VFTDKTSATVICRKNASISVRAQDRYYSSSWSEW
ASVPCS
(SEQ ID NO:9)

Figure 12

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSKAEKKDRVFTDKTSATVICRKNASISVRAQDRYYSSSWSEW
ASVPCS
(SEQ ID NO:10)

Figure 13

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSAAEKKDRVFTDKTSATVICRKNASISVRAQDRYYSSSWSEW
ASVPCS
(SEQ ID NO:11)

Figure 14

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSAREKKDRVFTDKTSATVICRKNASISVRAQDRYYSSSWSEW
ASVPCS
(SEQ ID NO: 12)

Figure 15

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSGREKKDRVFTDKTSATVICRKNASISVRAQDRYYSSSWSEW
ASVPCS
(SEQ ID NO: 13)

Figure 16

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSQREKKDRVFTDKTSATVICRKNASISVRAQDRYYSSSWSEW
ASVPCS
(SEQ ID NO:14)

Figure 17

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSKDEKKDRVFTDKTSATVICRKNASISVRAQDRYYSSSWSEW
ASVPCS
(SEQ ID NO:15)

Figure 18

IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSQDEKKDRVFTDKTSATVICRKNASISVRAQDRYYSSSWSEW
ASVPCS
(SEQ ID NO:16)

Figure 19

ATGTGTCACCAGCAGTTGGTCATCTCTTGGTTTTCCCTGGTTTTTCTGGCATCTCCCCTCGTGG
CCATATGGGAACTGAAGAAAGATGTTTATGTCGTAGAATTGGATTGGTATCCGGATGCCCCTGG
AGAAATGGTGGTCCTCACCTGTGACACCCCTGAAGAAGATGGTATCACCTGGACCTTGGACCAG
AGCAGTGAGGTCTTAGGCTCTGGCAAAACCCTGACCATCCAAGTCAAAGAGTTTGGAGATGCTG
GCCAGTACACCTGTCACAAAGGAGGCGAGGTTCTAAGCCATTCGCTCCTGCTGCTTCACAAAAA
GGAAGATGGAATTTGGTCCACTGATATTTTAAAGGACCAGAAAGAACCCAAAAATAAGACCTTT
CTAAGATGCGAGGCCAAGAATTATTCTGGACGTTTCACCTGCTGGTGGCTGACGACAATCAGTA
CTGATTTGACATTCAGTGTCAAAAGCAGCAGAGGCTCTTCTGACCCCCAAGGGGTGACGTGCGG
AGCTGCTACACTCTCTGCAGAGAGAGTCAGAGGGGACAACAAGGAGTATGAGTACTCAGTGGAG
TGCCAGGAGGACAGTGCCTGCCCAGCTGCTGAGGAGAGTCTGCCCATTGAGGTCATGGTGGATG
CCGTTCACAAGCTCAAGTATGAAAACTACACCAGCAGCTTCTTCATCAGGGACATCATCAAACC
TGACCCACCCAAGAACTTGCAGCTGAAGCCATTAAAGAATTCTCGGCAGGTGGAGGTCAGCTGG
GAGTACCCTGACACCTGGAGTACTCCACATTCCTACTTCTCCCTGACATTCTGCGTTCAGGTCC
AGGGCAAGAGCAAGAGAGAAAAGAAAGATAGAGTCTTCACGGACAAGACCTCAGCCACGGTCAT
CTGCCGCAAAAATGCCAGCATTAGCGTGCGGGCCCAGGACCGCTACTATAGCTCATCTTGGAGC
GAATGGGCATCTGTGCCCTGCAGTTAG
(SEQ ID NO:21)

Figure 20

GAATTCTCGGCAGGTGGAGGTCAGCTGGGAGTACCCTGACACCTGGAGCACTCCACATTCCTAC
TTCTCCCTGACATTCTGCGTTCAGGTCCAGGGCAAGGACAATACGGAGAGAGTGTTCACGGACA
AGACCTCAGCttttttttttttttgaagactcAATTCTCGGCAGGTGGAGGTCAGCTGGGAGTA
CCCTGACACCTGGAGTACTCCACATTCCTACTTCTCCCTGACATTCTGCGTTCAGGTCCAGGGC
AAGGACAATACGGAGGGTAGAGTGTTCACGGACAAGACCTCAGC
(SEQ ID NO:22)

Figure 21

GAATTCTCGGCAGGTGGAGGTCAGCTGGGAGTACCCTGACACCTGGAGCACTCCACATTCCTAC
TTCTCCCTGACATTCTGCGTTCAGGTCCAGGGCCAGGATCAGGACGAGAAGAAGGATAGAGTCT
TCTTTTTTTTTTgaagactcAATTCTCGGCAGGTGGAGGTCAGCTGGGAGTACCCTGACACCTG
GAGTACTCCACATTCCTACTTCTCCCTGACATTCTGCGTTCAGGTCCAGGGCCAGGATCAGGAC
GAGTCCGGAGATAGAGTCTTC
(SEQ ID NO:23)

Figure 22

GAATTCTCGGCAGGTGGAGGTCAGTTGGGAGTACCCTGACACCTGGAGCACTCCACATTCCTAC
TTCTCCCTGACATTCTGCGTTCAGGTCCAGGGCAAGAGCAAGGCAGAAAAGAAAGATAGAGTCT
TCACGGACAAGACCTCAGCtttttttttttgaagactcAATTCTCGGCAGGTGGAGGTCAGTTG
GGAGTACCCTGACACCTGGAGTACTCCACATTCCTACTTCTCCCTGACATTCTGCGTTCAGGTC
CAGGGCAAGAGCGCAGCTGAAAAGAAAGATAGAGTCTTTACGGACAAGACCTCAGC
(SEQ ID NO:24)

Figure 23

GAATTCTCGGCAGGTGGAGGTCAGTTGGGAGTACCCTGACACCTGGAGCACTCCACATTCCTAC
TTCTCCCTGACATTCTGCGTTCAGGTCCAGGGCAAGAGCGCCCGGGAAAAGAAAGATAGAGTCT
TCACGGACAAGACCTCAGCtttttttttttgaagactcAATTCTCGGCAGGTGGAGGTCAGTTG
GGAGTACCCTGACACCTGGAGTACTCCACATTCCTACTTCTCCCTGACATTCTGCGTTCAGGTC
CAGGGCAAGAGCGGTAGAGAAAAGAAAGATAGAGTCTTTACGGACAAGACCTCAGC
(SEQ ID NO:25)

Figure 28

IWELKKDVYVVELDWYPNAPGETVVLTCDTPEEDGITWTSDQSSEVLGTGKTLTIHVKEFGDAG
QYTCRKGGEALSRSLLLLHKKEDGIWSTDILKDQKEPKNKSFLKCEAKNYSGRFTCWWLTTIST
DLKFSVKSSRGSTDPRGVTCGTATLSEDLGEYKKYRVECQEGSACPAAEESLPIEVVLEAVHKL
KYENYTSSFFIRDIIKPDPPKNLQLKPLKNSRHVEVSWGYPDTWSTPHSYFSLTFCIQVQGKSK
REKKDRIFTDKTSATVICRKNAKIRVQARDRYYSSFWSEWASVSCS
(SEQ ID NO:44)

METHODS OF TREATING CANCER USING INTERLEUKIN-12P40 VARIANTS HAVING IMPROVED STABILITY

CROSS-REFERENCE TO RELATED APPLICATION

This application is a divisional application of U.S. application Ser. No. 12/961,733, filed Dec. 7, 2010, which is a divisional application of U.S. application Ser. No. 11/647,661, filed Dec. 29, 2006, which claims priority to and the benefit of U.S. Provisional Patent Application No. 60/755,382, filed Dec. 30, 2005, the entire disclosures of each of which are incorporated by reference herein.

FIELD OF THE INVENTION

This invention relates generally to IL-12p40 proteins, including fusion proteins containing IL-12p40, modified to improve their stability. In particular, the IL-12p40 proteins of the invention remove a proteolytic site in the region of Lys260 and Arg261 in the p40 subunit.

BACKGROUND OF THE INVENTION

Interleukin-12 (IL-12) is an inflammatory cytokine that is produced in response to infection by a variety of cells of the immune system, including phagocytic cells, B cells and activated dendritic cells (Colombo and Trinchieri (2002), *Cytokine & Growth Factor Reviews,* 13: 155-168). IL-12 plays an essential role in mediating the interaction of the innate and adaptive arms of the immune system, acting on T-cells and natural killer (NK) cells, enhancing the proliferation and activity of cytotoxic lymphocytes and the production of other inflammatory cytokines, especially interferon-γ (IFN-γ).

IL-12 is a heterodimeric molecule composed of an α-chain (the p35 subunit, IL-12p35) and a β-chain (the p40 subunit, IL-12p40) covalently linked by a disulfide bridge to form the biologically active 74 kDa heterodimer. Amino acid sequences of IL-12p35 and IL-12p40 of a mature (wild-type) human IL-12 are depicted in FIGS. 1 (SEQ ID NO:1) and 2 (SEQ ID NO:2), respectively.

Interleukin-23 (IL-23) is a disulfide-bridged heterodimeric molecule closely related to IL-12, in that it has the same β chain IL-12p40 as IL-12, but a unique a chain (the p19 subunit, IL-23p19) (Oppmann et al., (2000), *Immunity,* 13: 715-725). Like IL-12, IL-23 is produced by phagocytic cells and activated dendritic cells, and is believed to be involved in the recruitment and activation of a range of inflammatory cells (Langrish et al., (2004) *Immunol. Rev.,* 202: 96-105). The amino acid sequence of IL-23p19 of a mature human IL-23 is depicted in FIG. 3 (SEQ ID NO:3).

For immune cells to secrete biologically active IL-12 or IL-23 heterodimers, concomitant expression of the α and β subunits in the same cell is required. Secretion by immune cells of the IL-12p35 or IL-23p19 alone has not been observed, whereas cells that produce the biologically active IL-12 or IL-23 heterodimer secrete the p40 subunit in free form in 10 to 100-fold excess over the heterodimer (D'Andrea et al. (1992), *J. Exp. Med.,* 176: 1387-98, Oppmann et al., (2000), *Immunity,* 13: 715-725). In addition, it has been observed in the mouse that, even in the absence of an a subunit, cells may produce a biologically active IL-12p40 homodimer (Hikawa et al. (2004), *Neuroscience,* 129: 75-83).

The presence of endogenous IL-12 has been shown to be necessary for immunological resistance to a broad array of pathogens, as well as to transplanted and chemically induced tumors (Gateley et al. (1998), *Annu. Rev. Immunol.,* 16: 495-521). IL-12 has been demonstrated to have a potent anti-tumor activity based upon the induction of IFN-γ and the activation of effector cells such as CD8+ T-cells and NK cells (Brunda et al. (1993), *J. Exp. Med.,* 178: 1223-30). As a result of its demonstrated anti-tumor activity, IL-12 has been tested in human clinical trials as an immunotherapeutic agent for the treatment of a wide variety of cancers (Atkins et al. (1997), *Clin. Cancer Res.,* 3: 409-17; Gollob et al. (2000), *Clin. Cancer Res.,* 6: 1678-92; and Hurteau et al. (2001), *Gynecol. Oncol.,* 82: 7-10), including renal cancer, colon cancer, ovarian cancer, melanoma and T-cell lymphoma, and as an adjuvant for cancer vaccines (Lee et al. (2001), *J. Clin. Oncol.* 19: 3836-47).

For IL-12 or IL-23, production of the recombinant protein in its correctly folded and biologically active, heterodimeric form, requires the concurrent expression of both the a subunit and IL-12p40 in the producing cell line. The purified recombinant protein, however, exhibits a degree of heterogeneity resulting from proteolytic cleavage in the C-terminal region of the IL-12p40. The instability of the IL-12 or IL-23 protein can give rise to problems in its production and clinical use as a therapeutic agent. Therefore, there is a need in the art for improved recombinant IL-12 or IL-23 variants that yield a homogeneous protein more resistant to proteolytic cleavage.

SUMMARY OF THE INVENTION

The invention provides variants of human IL-12 p40 subunits (p40 variants) which have improved stability compared to wild-type IL-12 p40 proteins. In these p40 variants, the C-terminal region, which is normally sensitive to proteolytic cleavage, has been engineered to be more resistant to digestion by proteases. Specifically, p40 variants of the invention include engineered amino acid alterations in the D3 domain aimed to avoid the creation of potential T-cell epitopes that could make the variant proteins immunogenic and trigger antibody responses in humans. As a result, p40 variants of the invention have improved properties as therapeutic agents over wild-type IL-12p40 proteins with regard to their production, formulation, and pharmacokinetics.

Accordingly, in one aspect, the invention provides a variant of a human IL-12 p40 D3 domain (D3 variant), wherein the D3 variant has at least 85% identity with a wild-type human IL-12p40 D3 domain and includes an amino acid alteration at one or more positions corresponding to residues 258-266 of mature human IL-12 p40. Certain embodiments of the invention are based, in part, on an appreciation that an amino acid alteration or alterations according to the invention have the particular benefit of removing the proteolytic site between Lys260 and Arg261.

According to the invention, the amino acid alterations to one or more positions corresponding to residues 258-266 may be deletions, substitutions, or insertions. Moreover, amino acid substitutions that replace basic amino acids with non-basic amino acids can be used to create variants according to the invention.

In particular, D3 variants of the invention may include one or more amino acid substitutions at positions selected from the group consisting of Lys258, Ser259, Lys260, Arg261, Lys263, Lys264, Asp265, and Arg266. Such amino acid alterations can be used singly or in combination to induce the structural and/or functional changes described above. For example, the D3 variant can incorporate one, two, three, four or more of the following substitutions: Lys258Gln, Ser259Asp, Lys260Ala, Lys260Asn, Lys260Gln, Lys260Gly, Arg261Ala, Arg261Asp, Arg261Thr, Lys263Gly, Lys263Ser, and/or Lys264Gly.

In some embodiments, the substitution is a position Lys260. The substitution may replace Lys260 with a non-basic amino acid, for example, Ala, Asn, Gln, or Gly. Further substitutions in addition to Lys260 may occur at Ser259 and Arg261. Particularly, some D3 variants of the invention incorporate substitutions Ser259Asp, Lys260Asn, and Arg261Thr. In a further embodiment, D3 variants of the invention incorporate substitutions Ser259Asp, Lys260Asn, Arg261Thr and Lys264Gly, while optionally deleting Lys263 and Asp265. Alternately, a D3 variant of the invention incorporates substitutions Ser259Asp, Lys260Asn, Arg261Thr, and Lys264Gly while deleting Lys263, Lys264 and Asp265.

In other embodiments according to the invention, a D3 variant including a substitution replacing Lys260 alternatively includes further substitutions at one or more of Lys258, Ser259, Arg261, Lys263, and Lys264. For example, in one embodiment, a D3 variant includes the substitutions Lys258Gln, Ser259Asp, Lys260Gln, Arg261Asp, and optionally Lys263Ser and Lys264Gly.

In further embodiments, in addition to substitutions at Ser259, Lys260, and Arg261, one or more of residues corresponding to Lys263, Lys264, Asp265, and Arg266 are deleted, while in another embodiment, one or more of Lys263, Lys264, Asp265, and Arg266 are substituted with a non-basic amino acid. In a further embodiment, the substitution at Lys264 is Lys264Gly and, optionally, Lys263 and Asp265 are deleted. Other D3 variants of the invention incorporate substitutions Ser259Asp, Lys260Asn, Arg261Thr, and Lys264Gly, and optionally, deletion of residues corresponding to Lys263, Asp265 and Arg266.

It will be understood by those skilled in the art that p40 variants and active portions thereof that incorporate a D3 variant as described herein are within the scope of the invention. Similarly, IL-12 proteins and active portions thereof that contain a p40 variant (IL-12 variants) also are within the scope of the invention. The invention further encompasses fusion proteins including IL-12 variants of the invention and a moiety selected from the group consisting of an antibody moiety, a non-IL-12 cytokine, or an active portion thereof.

Similarly, IL-23 proteins and active portions thereof that contain a p40 variant (IL-23 variants) also are within the scope of the invention. The invention further encompasses fusion proteins including IL-23 variants of the invention and a moiety selected from the group consisting of an antibody moiety, a non-IL-23 cytokine, or an active portion thereof.

In another aspect, the invention relates to a nucleic acid that encodes any of the D3 variants, p40 variants, IL-12 variants, and IL-23 variants of the invention. The invention further encompasses a cell, e.g., a prokaryotic cell, including such a nucleic acid.

The invention also features methods of making such D3 variants, p40 variants, IL-12 variants, IL-23 variants and fusion proteins containing these moieties.

In yet another aspect, the invention provides methods of using the variants of the invention and the nucleic acids encoding same. For example, the invention encompasses a method of treating a patient that includes administering to the patient a therapeutically effective amount of a p40 variant of the invention or an active portion thereof.

The foregoing, and other features and advantages of the invention as well as the invention itself, will be more fully understood from the following figures, description, and claims.

BRIEF DESCRIPTION OF THE DRAWINGS

FIG. 1 depicts the mature amino acid sequence of the a chain, i.e., the p35 subunit, of a mature (wild-type) human IL-12 (SEQ ID NO:1).

FIG. 2 depicts the mature amino acid sequence of the β chain, i.e., the p40 subunit, of a mature (wild-type) human IL-12 (SEQ ID NO:2). Domain D3, corresponding to positions 211-306 (SEQ ID NO:26), is italicized, and the peptide fragment corresponding to positions 258-266 is underlined (SEQ ID NO:5), with Lys260 and Arg261 highlighted in bold.

FIG. 3 depicts the mature amino acid sequence of the a chain, i.e., the p19 subunit, of a mature (wild-type) human IL-23 (SEQ ID NO:3).

FIG. 4A shows the SDS-PAGE gel for several purified batches of human IL-12 produced as antibody fusion proteins (lanes 1-8), while

FIG. 5 depicts the amino acid sequence of the C-terminal peptide fragment of mature (wild-type) human IL-12p40 subunit. The fragment starts at Arg261 (SEQ ID NO:4).

FIG. 6 depicts the amino acid sequence of a peptide fragment corresponding to positions 258-266 of a mature (wild-type) human IL-12p40 subunit (SEQ ID NO:5).

FIGS. 7.1 and 7.2 depict an amino acid sequence alignment of IL-12p40 subunits from various mammals including human, baboon (*Papio anubis*), rhesus monkey (*Macaca mulatta*), mangabey (*Cercocebus torquatos*), dog (*Canis familiaris*), cat (*Fells catus*), horse (*Equus caballus*), pig (*Sus scrofa*), cow (*Bos Taurus*), goat (*Capra hircus*), sheep (*Ovis aries*), deer (*Cervus elaphus*), water buffalo (*Bubalus bubalis*), hamster (*Mesocricetus auratus*), guinea pig (*Cavia porcellus*), cotton rat (*Sigmodon hispidus*), rat (*Rattus norvegicus*), and mouse (*Mus musculus*). The two amino acids in bold indicate the proteolytic cleavage site.

FIG. 8 depicts the amino acid sequence of a variant, referred to herein as p40V1, of a mature human IL-12p40 subunit (SEQ ID NO:6). The engineered sequence is underlined.

FIG. 9 depicts the amino acid sequence of a variant, referred to herein as p40V2, of a mature human IL-12p40 subunit (SEQ ID NO:7). The engineered sequence is underlined.

FIG. 10 depicts the amino acid sequence of a variant, referred to herein as p40V3, of a mature human IL-12p40 subunit (SEQ ID NO:8). The engineered sequence is underlined.

FIG. 11 depicts the amino acid sequence of a variant, referred to herein as p40V4, of a mature human IL-12p40 subunit (SEQ ID NO:9). The engineered sequence is underlined.

FIG. 12 depicts the amino acid sequence of a variant, referred herein as p40V5, of a mature human IL-12p40 subunit (SEQ ID NO:10). The alteration is underlined.

FIG. 13 depicts the amino acid sequence of a variant, referred herein as p40V6, of a mature human IL-12p40 subunit (SEQ ID NO:11). The alterations are underlined.

FIG. 14 depicts the amino acid sequence of a variant, referred herein as p40V7, of a mature human IL-12p40 subunit (SEQ ID NO:12). The alteration is underlined.

FIG. 15 depicts the amino acid sequence of a variant, referred herein as p40V8, of a mature human IL-12p40 subunit (SEQ ID NO:13). The alteration is underlined.

FIG. 16 depicts the amino acid sequence of a variant, referred herein as p40V9, of a mature human IL-12p40 subunit (SEQ ID NO:14). The alteration is underlined.

FIG. 17 depicts the amino acid sequence of a variant, referred herein as p40V10, of a mature human IL-12p40 subunit (SEQ ID NO:15). The alteration is underlined.

FIG. 18 depicts the amino acid sequence of a variant, referred herein as p40V11, of a mature human IL-12p40 subunit (SEQ ID NO:16). The alterations are underlined.

FIG. 19 depicts the nucleic acid sequence encoding the full length (wild-type) human IL-12p40 subunit (SEQ ID NO:21).

FIG. 20 depicts the nucleic acid sequence of a synthetic nucleotide fragment, referred to herein as V1V2, encoding portions of p40 variants p40V1 and p40V2. The V1V2 fragment encompasses a V1 fragment including a region (underlined) encoding SEQ ID NO:17. This is followed by a linker sequence (lower case), and subsequently, a V2 fragment including a region (underlined) encoding SEQ ID NO:18.

FIG. 21 depicts the nucleic acid sequence of a synthetic nucleotide fragment, referred to herein as V3V4, encoding portions of p40 variants p40V3 and p40V4. The V3V4 fragment encompasses a V3 fragment including a region (underlined) encoding SEQ ID NO:19. This is followed by a linker sequence (lower case), and subsequently, a V4 fragment including a region (underlined) encoding SEQ ID NO:20.

FIG. 22 depicts the nucleic acid sequence of a synthetic nucleotide fragment, referred herein as V5V6, encoding portions of p40 variants p40V5 and p40V6. The V5V6 fragment encompasses a V5 fragment including a codon substitution (underlined) encoding Arg261Ala. This is followed by a linker sequence (lower case), and subsequently, a V6 fragment including codon substitutions (underlined) encoding Lys260Ala and Arg261Ala.

FIG. 23 depicts the nucleic acid sequence of a synthetic nucleotide fragment, referred herein as V7V8, encoding portions of p40 variants p40V7 and p40V8. The V7V8 fragment encompasses a V7 fragment including a codon substitution (underlined) encoding Lys260Ala. This is followed by a linker sequence (lower case), and subsequently, a V8 fragment including a codon substitution (underlined) encoding Lys260Gly.

FIG. 28 is an IL-12p40 variant having mutations outside the D3 region of the protein.

DETAILED DESCRIPTION OF THE INVENTION

Figure 4A:
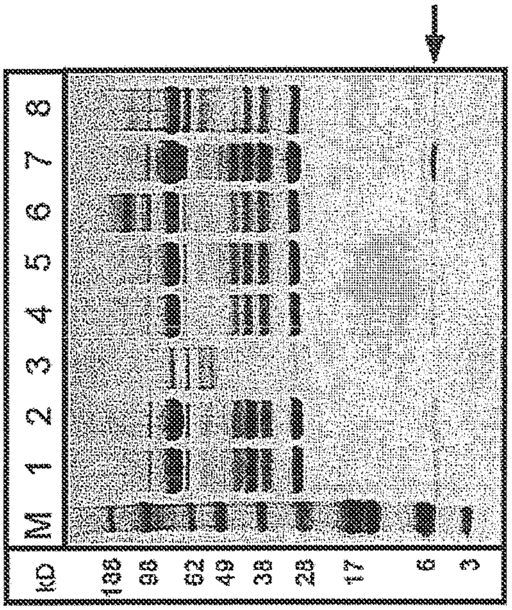

The invention describes variants of the cytokine interleukin-12 (IL-12) p40 subunit which have improved stability compared with the wild-type protein. In these variants, a region of the p40 subunit which is normally unstructured and sensitive to proteolytic cleavage is mutated to be more resistant to proteolytic cleavage. This region, in domain D3, is near the C-terminus of the p40 subunit, encompassing a polypeptide stretch corresponding to amino acids 258-266 in mature human p40 (p40(258-266)).

The IL-12p40 subunit is also a component subunit of the cytokine interleukin-23 (IL-23). IL-23 has two subunits, the a subunit "p19" and the β subunit "p40." The p40 subunit of IL-23 is the same as IL-12p40. Therefore, variants of IL-12p40 subunit are likewise variants of the IL-23p40 subunit.

In one general class of embodiments, one or more mutations are introduced into the region of p40 corresponding to amino acid residues 258-266 to eliminate the cleavage site, which in human p40 corresponds to the site between Lys260 and Arg261. In further embodiments, specific mutations are introduced in this region that by modeling generate a more tightly folded structure. In another aspect of the invention, the introduced mutations additionally are predicted to avoid making the engineered region of the p40 subunit immunogenic. For example, amino acid substitutions in the engineered region of the p40 subunit are chosen to avoid the creation of peptides that may be recognized as potential T-cell epitopes in humans.

Mutations may be introduced into the region of p40 corresponding to amino acid residues 258-266 by a variety of mechanisms. For example, in one embodiment, a mutation or mutations are introduced by substitution of one amino acid residue for another. In a further embodiment, a mutation or mutations are introduced by deletion of one or more residues of the p40 subunit. In yet another embodiment, a mutation or mutations are introduced by insertion of one or more amino acid residues into the p40 subunit.

In one embodiment, the p40 variants of the invention are contained in protein compositions such as IL-12 proteins, IL-12 fusion proteins, IL-23 proteins, IL-23 fusion proteins or p40 homodimers. For example, in one embodiment, an IL-12 protein contains a p35 subunit and a p40 variant according to the invention. In another embodiment, the IL-23 protein contains a p19 subunit and p40 variant according to the invention. In a further embodiment, a fusion protein contains an antibody portion fused to IL-12 containing an IL-12p40 variant. In an even further embodiment, a fusion protein contains an antibody portion fused to IL-23 containing an IL-12p40 variant. In a further embodiment, the antibody portion of the fusion protein is an intact antibody, an Fc region, an sc-Fv, an antigen binding portion of an antibody, or an active fragment of an antibody. In yet another embodiment, a fusion protein according to the invention includes an IL-12p40 variant fused to an non-IL-12 or non-IL-23 cytokine or active portion thereof.

In a further aspect of the invention, protein compositions that contain one of the p40 variants of the invention have a longer circulating half-life than the corresponding wild-type protein. Thus, in comparison with IL-12 or IL-23 proteins that contain the wild-type p40 subunit, IL-12 variants or IL-23 variants that include an engineered p40 subunit of the invention have improved properties as therapeutic agents with regard to their production, formulation and pharmacokinetics.

In a further embodiment, mutations to the IL-12p40 amino acid sequence are introduced outside the IL-12p40(258-266) region and optionally outside the IL-12p40 D3 domain of IL-12p40. Such mutations can be introduced elsewhere in the D3 domain of IL-12p40 and can be introduced in the other domains. For example, FIG. 28, depicts a sequence of a p40 subunit of IL-12 that has alterations in the amino acid sequence outside of residues 258-266. Leong et al., (2003), *Proc. Natl. Acad. Sci. USA,* 100:1163-1168, the contents of which are incorporated by reference herein, teach various residues which may be mutated in the IL-12 p40 amino acid sequence beyond the 258-266 region. Further, because the three dimensional crystal structure of IL-12p40 is known (Yoon et al., (2000), *EMBO J.,* 19:3530-3541, the contents of which are incorporated by reference herein), and residues essential to the interaction of the p40 subunit with the p35 subunit of IL-12 are know, selection of other mutations that will not destroy functionality of the p40 subunit are determinable by one of skill in the art.

Determination of the Cleavage Product

Figure 4B:
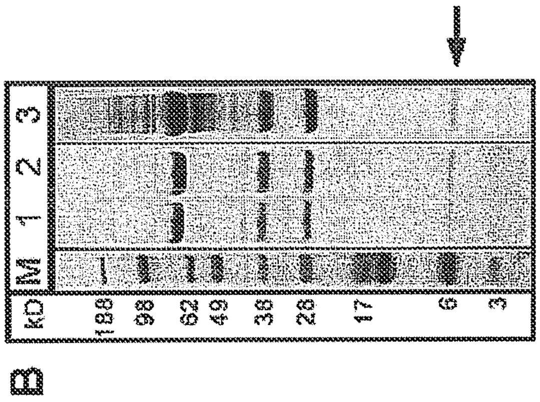
FIG. 4B shows the SDS-PAGE gel for several purified batches of human IL-23 produced as antibody fusion proteins (lanes 1-3). The IL-12p35 and IL-23p19 subunit is covalently attached to the antibody heavy chain. The 6 kD band is indicated by an arrow. Molecular weights (kD) are indicated for the markers (lane M).

The invention rests in part on the observation that the IL-12p40 subunit is susceptible to a specific proteolytic cleavage event, and on novel experimental results defining the cleavage site. It was found that a purified recombinant IL-12 protein, produced in NS/0 cells as described in Example 2, consistently exhibited a degree of heterogeneity when the recombinant protein was separated by electrophoresis on an SDS-PAGE gel under reducing conditions, clearly visible as an additional protein band of approximately 6 kD molecular weight. A similar observation was made for recombinant IL-23 protein. This is illustrated in FIG. 4 which shows the SDS-PAGE gel for several purified batches of human IL-12 (Panel A) and human IL-23 protein compositions (Panel B) produced as antibody fusion proteins.

The contaminant was purified and its amino acid sequence was determined, as described in Example 3, and was found to correspond to the sequence of the C-terminal 46 amino acid fragment of the IL-12p40 subunit itself, generated by proteolytic cleavage between Lys260 and Arg261 (FIG. 5—SEQ ID NO:4). Cleavage between Lys260 and Arg261 appears to be highly favored despite a prevalence of basic amino acids in the region surrounding the cleavage site ( . . . KSKREKKDR . . . (FIG. 6—SEQ ID NO:5) where Lys260 and Arg261 are indicated in bold). However, in spite of being cleaved from the p40 subunit, the C-terminal peptide fragment remains non-covalently associated with the rest of the p40 subunit, making it difficult to remove the resulting heterogeneity by further purification of the recombinant protein.

IL-12p40 Protein

The mature human p40 subunit is a 306 amino acid protein resembling a soluble class I cytokine a receptor, composed of domains D1, D2 and D3. The cleavage site (between Lys260 and Arg261) is within D3, a fibronectin type III domain of 96 amino acids encompassing the region from I211 to S306. The sequence for mature human IL-12 p40 subunit is shown in FIG. 2. The amino acid sequence for the D3 is shown in FIG. 2 in italics. In the published X-ray crystallographic structure of the human IL-12 heterodimer (Yoon et al. (2000), *EMBO J.,* 19: 3530-41) a portion of a loop within the region of human p40(258-266) of the D3 domain is not resolved. Without wishing to be bound by theory, unresolved regions in crystal structures are often an indication of flexible, unstructured loops, and may constitute target sites for proteolysis.

A primary structure alignment of the mature p40 subunit from a variety of mammalian species is shown in FIGS. 7.1 and 7.2, including human; the primates baboon, rhesus monkey and mangabey; dog; cat; horse; pig; the ruminants cow, goat, sheep, deer, water buffalo; and the rodents hamster, guinea pig, cotton rat, rat and mouse. In the alignment the region around p40(258-266) exhibits sequence variability, particularly with respect to its length. Particularly, in some species, notably ruminants, the sequence is shorter, and in others, such as in rodents, the sequence in some instances may contain an additional insert. In many species, the dipeptide motif corresponding to human p40 K260R261 is conserved, either identically or exhibiting two basic amino acids. These species include agriculturally and commercially important species including, but not limited to, the horse, cow, goat, pig, and sheep. Consequently, introducing one or more mutations into the region of non-human IL-12p40 corresponding to residues 258-266 of human IL-12p40 that are analogous to mutations taught herein with respect to human IL-12p40 may prove useful in reducing or eliminating proteolytic cleavage of non-human IL-12p40 at the K260R261 cleavage site.

In principle, according to the invention, it is possible to use a IL-12p40 variant from a species that lacks a positively charged dipeptide motif corresponding to human IL-12p40 K260R261 in a human or other heterologous organism. However, in practicing the invention, it is important to note that non-human forms of IL-12p40 will generally lead to anti-p40 antibodies when administered to humans. More broadly, it is not optimal to administer p40 from one species to another. In addition, the potential of various non-human p40 subunits to be proteolytically cleaved is generally unknown. In addition, p40 subunits from one species may not function in another species, either at the step of assembly with subunits such as p35 or p19, or at the step of interaction with receptor subunits.

Variant IL-12p40 Proteins

The invention provides for variant IL-12p40 proteins with mutations in the D3 domain that improve stability. As used herein, the term "D3 variant" refers to a D3 domain of a human p40 subunit of, for example, IL-12 or IL-23, having one or more amino acid alterations as compared to wild-type D3. The term "p40 variant" is used herein to refer to a human p40 subunit of, for example, IL-12 or IL-23, with mutations in the D3 domain, i.e., a p40 subunit containing a D3 variant. The term "IL-12 variant" is used herein to refer to a human IL-12 protein containing a p40 variant. The term "IL-23 variant" is used herein to refer to a human IL-23 protein containing a p40 variant.

According to one embodiment of the invention, the D3 domain of a p40 variant has at least 70% or more sequence identity with the D3 domain of wild-type IL-12p40. In a further embodiment, the D3 domain of a p40 variant has at least 75% or more sequence identity with the D3 domain of wild-type IL-12p40. In yet another embodiment, the D3 domain of a p40 variant has at least 80% or more sequence identity with the D3 domain of wild-type IL-12p40, while in further embodiments, the D3 domain of a p40 variant has at least 81% or more, or at least 82% or more, or at least 83% or more, or at least 84% or more, or at least 85% or more, or at least 86% or more, or at least 87% or more, or at least 88% or more, or at least 89% or more, or at least 90% or more, or at least 91% or more, or at least 92% or more, or at least 93% or more, or at least 94% or more, or at least 95% or more, or at least 96% or more, or at least 97% or more, or at least 98% or more, or at least 99% or more identity with the D3 domain of wild-type IL-12p40.

According to another embodiment of the invention, the amino acid sequence of a p40 variant has at least 70% or more sequence identity with the amino acid sequence of mature wild-type IL-12 p40. In a further embodiment, the amino acid sequence of a p40 variant has at least 75% or more sequence identity with the amino acid sequence of mature wild-type IL-12p40. In yet another embodiment, the amino acid sequence of a p40 variant has at least 80% or more sequence identity with the amino acid sequence of mature wild-type IL-12p40, while in further embodiments, the amino acid sequence of a p40 variant has at least 81% or more, or at least 82% or more, or at least 83% or more, or at least 84% or more, or at least 85% or more, or at least 86% or more, or at least 87% or more, or at least 88% or more, or at least 89% or more, or at least 90% or more, or at least 91% or more, or at least 92% or more, or at least 93% or more, or at least 94% or more, or at least 95% or more, or at least 96% or more, or at least 97% or more, or at least 98% or more, or at least 99% or more identity with the amino acid sequence of mature wild-type IL-12p40.

To determine the percent identity between two amino acid sequences, the sequences are aligned for optimal comparison purposes (e.g., gaps can be introduced in the sequence of a first amino acid sequence for optimal alignment with a second amino acid sequence). The percent identity between the two sequences is a function of the number of identical positions shared by the sequences (i.e., % identity=(# of identical positions/total # of positions)times 100). If the sequences being compared are of unequal length, the shorter of the sequences is used to determine the total number of positions. The determination of percent identity between two sequences can also be accomplished using a mathematical algorithm.

A non-limiting example of a mathematical algorithm utilized for the comparison of two sequences is the algorithm of Karlin and Altschul, (1990) *Proc. Natl. Acad. Sci. USA,* 87:2264-68, modified as in Karlin and Altschul, (1993) *Proc. Natl. Acad. Sci. USA,* 90:5873-77. Such an algorithm is incorporated into the NBLAST and XBLAST programs of Altschul et al., (1990) *J. Mol. Biol.,* 215:403-10. BLAST nucleotide searches can be performed with the NBLAST program, score=100, wordlength=12. BLAST protein searches can be performed with the XBLAST program, score=50, wordlength=3. To obtain gapped alignments for comparison purposes, Gapped BLAST can be utilized as described in Altschul et al., (1997) *Nucleic Acids Research,* 25(17):3389-3402. When utilizing BLAST and Gapped BLAST programs, the default parameters of the respective programs (e.g., XBLAST and NBLAST) can be used.

In one embodiment, the invention provides D3 variants containing an alteration that removes the proteolytic cleavage site between Lys260 and Arg261. In one embodiment, the amino acid at position Lys260 is mutated. In a more specific embodiment, Lys260 is replaced with a non-basic amino acid. Non-basic amino acids include, for example, Ala, Asn, Asp, Cys, Glu, Gln, Gly, Ile, Leu, Met, Phe, Pro, Ser, Thr, Trp, Tyr, or Val. For example, Lys260 is replaced with either Ala, Asn, Asp, Cys, Glu, Gln, Gly, Ile, Leu, Met, Phe, Pro, Ser, Thr, Trp, Tyr, or Val. In an alternate embodiment, Lys260 is replaced with selenocysteine. Examples of D3 variants where Lys260 has been replaced by another amino acid are shown in FIGS. 12, 13, 14, 15, 16, and 18.

In another embodiment, Arg261 is mutated. For example, in one embodiment, Arg261 is replaced with any non-basic amino acid. For example, in one embodiment, Arg261 is replaced with Ala, Asn, Asp, Cys, Glu, Gln, Gly, Ile, Leu, Met, Phe, Pro, Ser, Thr, Trp, Tyr, or Val. In an alternate embodiment, Arg261 is replaced with selenocysteine. Examples of D3 variants where Arg261 has been replaced by another amino acid are shown in FIGS. 12, 13, 17, and 18. In a further embodiment, Lys260 and Arg261 are mutated. For example, in one embodiment, Lys260 and Arg261 are each replaced with another amino acid. For example, Lys260 is replaced with either Gln, Ala, Asn, or Gly and Arg261 is replaced with either Ala, Asp, or Thr. Examples of D3 variants where both Lys260 and Arg261 have been replaced by other amino acids are shown in FIGS. 13 and 18.

In addition, Lys260 and Arg261 are deleted in one embodiment, while in a further embodiment, an amino acid is inserted between Lys260 and Arg261.

In a further embodiment, a D3 variant is created in which one or more of Lys258, Ser259, Lys260, Arg261, Lys263, Lys264, or Arg266 is each replaced by another amino acid. In one embodiment, one or more of Lys258, Ser259, Lys260, Arg261, Lys263, Lys264, or Arg266 is each replaced by a non-basic amino acid. For example, in one embodiment, Lys258 is replaced with Gln. In another embodiment, Ser259 is replaced with Asp. In another embodiment, Lys260 is replaced with Ala, Gly, Asn or Gln. In a further embodiment, Arg261 is replaced with Ala, Thr or Asp. In yet another embodiment, Lys263 is replaced by Ser. In a further embodiment, Lys264 is replaced by Gly. In one embodiment, Arg266 is replaced with Gln, Asp, Asn, or Thr. In a further embodiment, Lys263 and Lys264 are replaced each replaced by another amino acid. For example, in one embodiment Lys263 and Lys264 are each replaced by Ser and Gly respectively. In yet another embodiment, Lys258, Ser259, Lys260, Arg261, Lys263, and Lys264 are replaced by Gln, Asp, Gln, Asp, Ser and Gly respectively.

In a further embodiment, a D3 variant is created in which one or more of Ser259, Lys260, and Arg261 are each replaced by another amino acid. In a further embodiment, one or more of Ser259, Lys260, and Arg261 are each replaced by a non-basic amino acid. For example, in one embodiment, Ser259, Lys260, and Arg261 are replaced by Asp, Asn, and Thr respectively.

In another embodiment, Lys258, Ser259, Lys260, and Arg261 are each replaced by another amino acid. For example, in one embodiment, Lys258, Ser259, Lys260, and Arg261 are each replaced by a non-basic amino acid. In one embodiment, Lys258, Ser259, Lys260, and Arg261 are each replaced by Gln, Asp, Gln, and Asp respectively. In a further embodiment, Ser259, Lys260, Arg261 and Lys264 are replaced by Asp, Asn, Thr, and Gly respectively. In yet a further embodiment, Ser259, Lys260, Arg261 and Lys264 are replaced by Asp, Asn, Thr, and Gly respectively, while Lys263, and Asp265 are deleted. In yet another embodiment, Ser259, Lys260, and Arg261 are each replaced by Asp, Asn, and Thr respectively, while Lys263, Lys264, and Asp265 are deleted.

Without wishing to be bound by theory, deletions are believed to have the effect of reducing the conformational flexibility of the p40(258-266) region, thus reducing the ability of the Lys260-Arg261 motif to adopt a conformation that allows cleavage by the relevant protease. Therefore, in one embodiment, one or more of Lys258, Ser259, Lys260, Arg261, Lys263, Lys264, Asp265, or Arg266 is deleted.

In a further embodiment, a D3 variant is created in which one or more of Lys263, Lys264, Asp265, or Arg266 is deleted. For example, in one embodiment, Lys263 and Asp265 are deleted, while in another embodiment, Lys263, Lys264, and Asp265 are deleted. In another embodiment, Lys263, Lys264, and Asp265 are deleted and replaced by one or more non-basic amino acids. In a further embodiment, Lys263, Lys264, Asp265, and Arg266 are deleted. In a further embodiment, one or more of Lys263, Lys264, Asp265 or Arg266 is deleted, while one or more of Ser259, Lys260, or Arg261 is replaced by another amino acid. For example, in one embodiment, Ser259, Lys260, and Arg261 are replaced by Asp, Asn, and Thr respectively while Lys263, Lys264 and Asp265 are deleted. In a further embodiment, Ser259, Lys260, and Arg261 are replaced by Asp, Asn, and Thr respectively while Lys263, Lys264, Asp265, and Arg266 are deleted.

In other embodiments, the amino acid substitutions are selected such that they avoid creating novel T-cell epitopes. Methods to analyze peptide sequences for their potential to create T-cell epitopes are well known in the art (see, e.g., U.S. Patent Application Publication No. 2003/0153043; International Publication No. WO 00/034317; and Sturniolo et al. (1999), Nature Biotech., 17: 555-61). In one embodiment, the sequence of human IL-12p40(258-266) is replaced by the sequence KDNTER (SEQ ID NO:17). In other words, Ser259, Lys260, and Arg261 were replaced by Asp, Asn, and Thr respectively while Lys263, Lys264, and Asp265 were deleted such that the resulting sequence from residue 258-263 in the variant is KDNTER. The resulting IL-12p40 variant is shown in FIG. 8.

In another embodiment, the sequence of human IL-12p40 (258-266) is replaced by the sequence KDNTEGR (SEQ ID NO:18). In other words, Ser259, Lys260, and Arg261 were replaced by Asp, Asn, and Thr respectively while Lys263, Lys264 and Asp265 were deleted and replaced by only a Gly residue such that the resulting sequence from residue 258-264 in the variant is KDNTEGR. The resulting IL-12p40 variant is shown in FIG. 9.

In yet another embodiment, the sequence of human IL-12p40(258-266) is replaced by the sequence QDQDEKKDR (SEQ ID NO:19). In other words, Lys258, Ser259, Lys260, and Arg261 were replaced by Gln, Asp, Gln, and Asp respectively, such that the resulting sequence from residue 258-266 in the variant is QDQDEKKDR. The resulting IL-12p40 variant is shown in FIG. 10.

In a further embodiment, the sequence of human IL-12p40 (258-266) is replaced by the sequence QDQDESGDR (SEQ ID NO:20). In other words, Lys258, Ser259, Lys260, Arg261, Lys263, and Lys264 were replaced by Gln, Asp, Gln, Asp, Ser, and Gly respectively such that the resulting sequence from residue 258-266 is QDQDESGDR. The resulting IL-12p40 variant is shown in FIG. 11.

In a further embodiment, a D3 variant is contained within an IL-12p40 subunit or active portion thereof. By active portions, it is meant that an IL-12p40 subunit containing a D3 variant has at least 10% activity in one embodiment, at least 20% in another embodiment, at least 30% in another embodiment, at least 50% activity in another embodiment, at least 70% activity in another embodiment, at least 75% activity in another embodiment, at least 80% activity in another embodiment, at least 90% activity in another embodiment, at least 95% activity in another embodiment, at least 99% activity in a further embodiment, at least 100% activity in another embodiment, at least 150% activity in a further embodiment, at least 200% activity in another embodiment, at least 300% activity in a further embodiment, at least 400% activity in another embodiment, at least 500% activity in another embodiment, or at least 1000% activity in another embodiment, in comparison to the biological activity of a wild type IL-12p40 moiety.

Proteins Containing IL-12p40 Variants

The IL-12p40 variants may be introduced into protein compositions in place of wild-type IL-12p40. Examples of biologically active protein compositions that include IL-12p40 are p40 homodimers, IL-12 and IL-12 fusion proteins, and IL-23 and IL-23 fusion proteins. In one aspect of the invention, the IL-12 p35/variant p40 heterodimer consists of separate polypeptide chains. Alternatively, the IL-12 p35/variant p40 heterodimer consists of a single polypeptide chain. In another aspect of the invention, the IL-23 p19/variant p40 heterodimer consists of separate polypeptide chains. Alternatively, the IL-23 p19/variant p40 heterodimer consists of a single polypeptide chain.

In another aspect of the invention, as part of an IL-12 fusion protein, the IL-12 fusion partner can be an antibody moiety or part of an antibody moiety. Useful antibody moieties include ones that target the IL-12 fusion protein to the tumor environment, for example to the tumor cells themselves, or to the necrotic core of a tumor or to the supporting stroma. In another embodiment of the invention, the fusion partner is another cytokine. Useful cytokines include, but are not limited to, IL-2, IL-7, and IL-15.

In another aspect of the invention, as part of an IL-23 fusion protein, the IL-23 fusion partner can be an antibody moiety or part of an antibody moiety. Useful antibody moieties include ones that target the IL-23 fusion protein to the tumor environment, for example to the tumor cells themselves, or to the necrotic core of a tumor or to the supporting stroma. In another embodiment of the invention, the fusion partner is another cytokine. Useful cytokines include, but are not limited to, IL-2, IL-7, and IL-15.

Nucleic Acids Encoding p40 Variants

In a further aspect of the invention, nucleic acids encoding polypeptides containing p40 variants of the invention are contemplated. Nucleic acids encoding p40 variants of the invention can be constructed, for example, using DNA techniques familiar to those skilled in the art. Exemplary procedures can be found in Example 1.

FIG. 19 depicts the nucleic acid sequence encoding mature human IL-12p40 subunit. FIGS. 20-22 depict synthetic nucleotide fragments for encoding exemplary mutations found in p40 variants of the invention.

Methods of Treatment Using p40 Variants

The p40 variants, including fusion proteins and IL-12 proteins or IL-23 proteins containing a p40 variant, of the invention are useful as immunotherapeutic agents, such as for the treatment of a wide variety of cancers, based on the demonstrated anti-tumor activity of IL-12 proteins. For example, p40 variants of the invention can be used, preferably as a heterodimer with p35, in the treatment of cancers including but not limited to renal cancer, colon cancer, ovarian cancer, melanoma and T-cell lymphoma, and as an adjuvant for cancer vaccines. p40 variants can also be used as part of a p40/p40 homodimer to reduce a TH 1 response (e.g., a TH 1 response associated with an autoimmune disease).

Administration

Both IL-12 variants, IL-23 variants, and p40 variants of the invention can be incorporated into a pharmaceutical composition suitable for administration. Such compositions typically comprise IL-12 variant or a fusion protein containing an IL-12 variant and a pharmaceutically-acceptable carrier. As used herein, the term "pharmaceutically-acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Medicaments that contain IL-12 variants, IL-23 variants, or p40 variants of the invention can have a concentration of 0.01 or less to 100% (w/w), though the amount varies according to the dosage form of the medicaments.

Administration dose depends on the body weight of the patients, the seriousness of the disease, the particular type of IL-12p40 variant being used, and the doctor's opinion. For example, for an IL-12 variant of the invention, it is generally advisable to administer between about 0.01 to about 10 mg/kg body weight a day, about 0.02 to about 2 mg/kg/day in case of injection, or about 0.5 mg/kg/day. The dose can be administered once or several times daily according to the seriousness of the disease and the doctor's opinion. For an antibody-IL-12 fusion protein or antibody-IL23 fusion protein containing a IL-12p40 variant of the invention, it is generally advisable to administer between about 0.001 to about 1 mg/kg body weight per day, about 0.002 to about 0.5 mg/kg/day in case of injection, or about 0.1 mg/kg/day. The dose can be administered once or twice per 2, 3 or 4 week period, according to the nature and seriousness of the disease and the doctor's opinion.

Aspects of invention are further illustrated by the following examples.

EXAMPLES

Example 1

Cloning of Variants of Human IL-12p40 Subunits

Nucleic acids encoding p40 variants of the invention, in particular, p40V1 through p40V8 (SEQ ID NOS:6-13), were constructed using standard DNA techniques familiar to those skilled in the art. In essence, a DNA cassette, encoding a fragment that spans the region encompassing the mutated amino acid residues and that is bracketed by convenient restriction sites, was synthesized de novo (Blue Heron Biotechnology, Bothell, Wash.), and substituted for the corresponding fragment of wild-type sequence contained in an expression plasmid carrying the p40 sequence (see, e.g., pNC-p40 in U.S. Pat. No. 6,838,260). The nucleic acid sequence encoding mature (wild-type) human IL-12p40 subunit is shown in FIG. 19. Expression plasmids encoding the p40 variants were thus obtained.

In particular, the nucleic acids encoding p40V1 and p40V2 were generated as follows. A cloning vector carrying p40V1 and p40V2 DNA cassettes (pBHV1V2), synthesized as a contiguous fragment as shown in FIG. 20, was digested with Bpu10 I and either Eco RI/Sca I or Bbs I, generating an EcoR I/Bpu10 I (for V1) and Bbs I/Bpu10 I (for V2) cassette with EcoR I/Bpu10 I compatible ends, respectively. The Sca I digestion was included to eliminate the similarly sized V2 fragment. These purified fragments were cloned into a pNC-p40 expression vector in a triple ligation with the appropriate Bpu10 I/Pvu I and Pvu I/Eco RI fragments obtained from NC-p40.

An identical approach was used to generate nucleic acids encoding p40V5 and p40V6, starting with the synthesized sequence shown in FIG. 21, and to generate nucleic acids encoding p40V7 and p40V8, starting with the synthesized sequence shown in FIG. 23.

Similarly, to generate nucleic acids encoding p40V3 and p40V4, the plasmid (pBHV3V4) carrying the synthesized sequence shown in FIG. 22, was digested with EcoR I/Bbs I/Sca I (the Sca I digestion was included to eliminate the similarly sized V4 fragment), or with Bbs I alone, generating an EcoR I/Bbs I (for V3) and a Bbs I (for V4) cassette, respectively, each with ends compatible with the EcoR I/Bbs I digested expression plasmid pNC-p40. Note that for the Bbs I restriction enzyme the recognition and cleavage sequences are separate, and thus sequences containing multiple Bbs I recognition sites may generate different, sequence-specific overhangs. The V3 and V4 cassettes were then gel purified and ligated, respectively, into the expression plasmid pNC-p40 in a triple ligation using the appropriate Bbs I/Pvu I and Pvu I/Eco RI fragments obtained from pNC-p40.

The same general approach may be used to generate further nucleic acid molecules encoding other p40 variants contemplated by the invention.

Example 2

Expression of p40 Variants and of Antibody-IL12; Fusion Proteins Containing p40 Variants Standard methods were used to generate cell lines expressing p40 variants of the invention (see U.S. Pat. No. 6,838,260). The pNC-p40 expression plasmids encoding p40 variants were electroporated into cells, e.g., NS/0 cells. The cells were plated, and transfected cells were selected on a G418-containing medium. Culture supernatants from drug-resistant clones were assayed for production of p40 by ELISA, and the highest producers were subcloned and tested for stable expression.

To generate antibody-IL-12 fusion protein expressing cell lines with p40 variants of the invention, the sequential transfection approach described in U.S. Pat. No. 6,838,360 was followed. For example, the fusion protein DI-NHS-IL12p40V1 was obtained by further transfecting the cell line expressing p40V1 with a second plasmid, pdHL10lambdaDI-NHS-p35, which encodes the NHS76 antibody, wherein the C-terminus of the heavy chain constant region is connected to the N-terminus of the IL-12 p35 subunit. The expression plasmid pdHL10lambda is a derivative of pdHL7, wherein the encoded light chain constant domain is a lambda chain. The cells were selected on a methotrexate-containing medium, and stable transfectants expressing the antibody fusion proteins were cloned by standard methods.

Example 3

Purification and Characterization of p40 Variants

Figure 24:
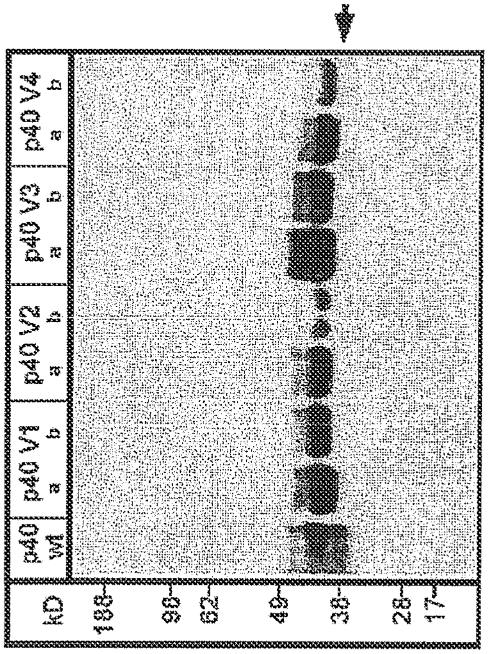
FIG. 24 is a Western blot with a polyclonal anti-hu-p40 antibody. Supernatants of cells transfected with wild-type IL-12p40 and IL-12p40 variants (V1-V4) were harvested and processed on an SDS-PAGE gel. Two independent clones (a, b) of each IL-12p40 variant p40V1, p40V2, p40V3, and p40V4 were tested. The arrow points to the band of cleaved IL12p40 lacking C-terminal fragment (lane p40 wt).

To characterize the integrity of p40 variants p40V1, p40V2, p40V3, and p40V4 (SEQ ID NO:6-9), spent cell culture media from duplicate transiently transfected NS-0 cells expressing these variants were collected, and processed for a Western blot with a polyclonal anti-hu-p40 antibody, shown in FIG. 24. The control wild-type p40 subunit was included as a control (lane 1). It was found that the cleaved species lacking the C-terminal 6 kDa fragment, which is normally well-resolved from the intact p40 species by these electrophoretic conditions (see arrow pointing to band in lane 1), was not present in any of the variants tested (lanes 2-9), and only intact p40 could be detected. Thus, the tested p40 variants were resistant to a proteolytic activity present during protein expression.

Antibody fusion proteins containing IL-12p40 variants were purified from cell culture supernatant using standard techniques based on Protein A capture (see U.S. Pat. No. 6,838,260).

Figure 25:
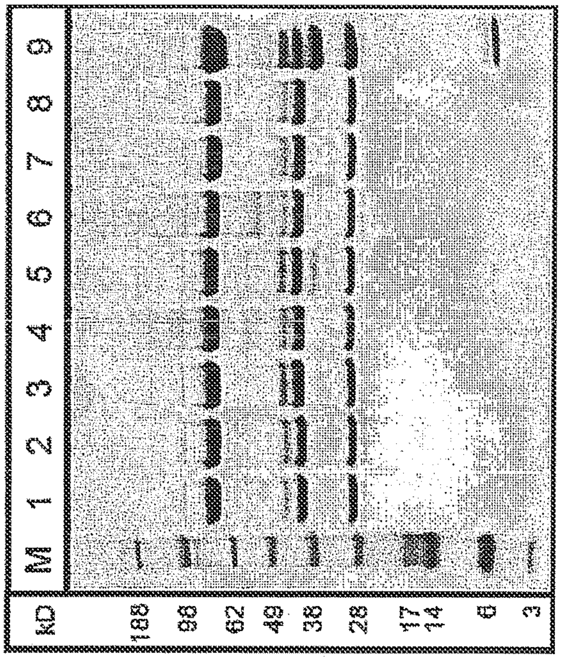
FIG. 25 shows the SDS-PAGE gel for antibody-IL12 fusion proteins containing p40 variants p40V1, p40V2, p40V3, p40V4, p40V5, p40V6, p40V7, p40V8, and wild type p40 (lanes 1-9). The upper most main band represents the fusion protein between the antibody heavy chain and the p35 subunit, and the lower main band represents the antibody light chain. The 6 kDa band was not detected in any of the lanes of the variant proteins, except lane 5. Molecular weights (kD) are indicated for the markers (lane M).

SDS-PAGE gel of the purified antibody fusion proteins from NS-0 stable clones of the p40 variants given in SEQ ID NOS:6-13 (lanes 1-8) and of the non-mutated control (lane 9) is shown in FIG. 25. The middle of the three major bands represents the non-cleaved p40 subunit, with the faint band slightly above indicating more glycosylated species. The upper most main band represents the fusion protein between the antibody heavy chain and the p35 subunit, and the lower main band represents the antibody light chain. It was found that, with the exception of the sample of the antibody fusion protein containing IL-12p40V5, the 6 kDa band was not present. For IL-12p40V5, a residual 6 kDa band was observed (lane 5).

Example 4

Characterization of a Proteolytic Cleavage Site in the Wild-Type IL-12p40 Subunit The identity of the contaminating approximately 6 kDa protein fragment was determined by standard methods. Briefly, purified DI-NHS-IL12 protein was denatured and reduced in a buffered 6 M guanidine/1 mM DTT solution at 55° C., and subjected to reverse phase HPLC separation over a Vydac C4 column with a 10% to 90% acetonitrile gradient. The fraction corresponding to the unidentified peptide species was collected, dried and re-suspended to run on an SDS-PAGE gel confirming that it corresponded to the 6 kDa fragment, and to determine the sequence of the peptide by N-terminal sequencing. The sequencing analysis revealed a peptide with the sequence REKKDRVFTD, which corresponds to a sequence in the mature (wild-type) human IL-12p40 subunit beginning at Arg261.

Example 5

Bioactivity of IL-12 Proteins Containing p40 Variants

Bioactivity of IL-12 proteins containing p40 variants was measured by induction of IFNγ from human PBMC. The antibody fusion proteins Ab-IL-12 containing variants p40V1 to p40V8 were compared to Ab-IL-12 with wild-type p40 and a recombinant human IL-12 protein.

The IFNγ induction assay was performed essentially as described in Gately et al. (1995), *Current Protocols in Immunology*, Section 6.16.4, and Kobayashi et al. (1989), *J. Exp Med.,* 170: 827-845. PBMCs were cultured with PHA-P for 3 days and then 25 IU/ml of hu IL-2 (R&D Systems, Minneapolis Minn.) was added for an additional 24 hours. The cells were washed, 20 IU/ml of IL-2 was added to all cells, followed by addition of IL-12 fusion proteins, with a series of two-fold dilution starting at 20 ng/ml (in terms of relative mass contribution of IL-12 to the molecule). Twenty-four hours later, the concentration of IFNγ was measured by ELISA using antibody pairs purchased from R&D Systems.

The results of two separate experiments using PBMCs from different donors are summarized Table 1.

TABLE 1

Bioactivity of Ab-IL12 variants in a IFNγ induction assay.

| | IFNγ Induction ED50 (ng/ml) | |
|---|---|---|
| Protein | AVG (n = 3) | SD |
| **Exp I** | | |
| R&D IL-12 | 0.04 | 0.02 |
| Ab-IL12 | 0.43 | 0.21 |
| Ab-IL12 V1 | 1.11 | 0.59 |
| Ab-IL12 V2 | 1.09 | 0.32 |
| Ab-IL12 V3 | 1.09 | 0.21 |
| Ab-IL12 V4 | 1.44 | 0.48 |
| **Exp II** | | |
| R&D IL-12 | 0.05 | 0.03 |
| Ab-IL12 | 0.53 | 0.42 |
| Ab-IL12 V1 | 1.53 | 0.58 |
| Ab-IL12 V4 | 1.79* | 0.80 |
| Ab-IL12 V5 | 0.58 | 0.39 |
| Ab-IL12 V6 | 1.63 | 1.46 |
| Ab-IL12 V7 | 0.99 | 1.27 |
| Ab-IL12 V8 | 0.74 | 0.68 |

*(n = 2)

Compared to recombinant hu IL-12, the activity of Ab-IL12 with wild type p40 was about 10 fold reduced. It was found that the antibody-IL12 variant proteins tested did not significantly further affect the activity of the protein. Ab-IL12p40V1 to Ab-IL12p40V8 had somewhat reduced activity (approximately 1.5-3 fold less) compared to the corresponding wild-type antibody-IL-12 fusion protein.

Example 6

Pharmacokinetics of IL-12 Proteins Containing p40 Variants

The pharmacokinetics of the antibody fusion proteins containing the p40 variants was determined. The experiments were performed using standard techniques familiar to those skilled in the art. Briefly, BALB/c mice (n=3 per treatment group) were injected with 25 μg of Ab-IL12 or Ab-IL12 variants containing the variants p40V1, p40V2, p40V3, p40V4, p40V5, p40V6, p40V7 and p40V8 in a volume of 0.2 ml, either intravenously in the tail vein or subcutaneously. At various time points up to 24 hours and up to 96 hours, respectively, small volumes of blood was taken by retro-orbital bleeding and collected in heparin-coated tubes to prevent clotting. After centrifugation to remove cells, the plasma was assayed by capture with anti-human IgG H&L antisera and detection with an anti-human IL-12 antibody. Results were normalized to the initial concentration in the plasma of each mouse taken within 30 seconds after injection (t=0).

Figure 26:
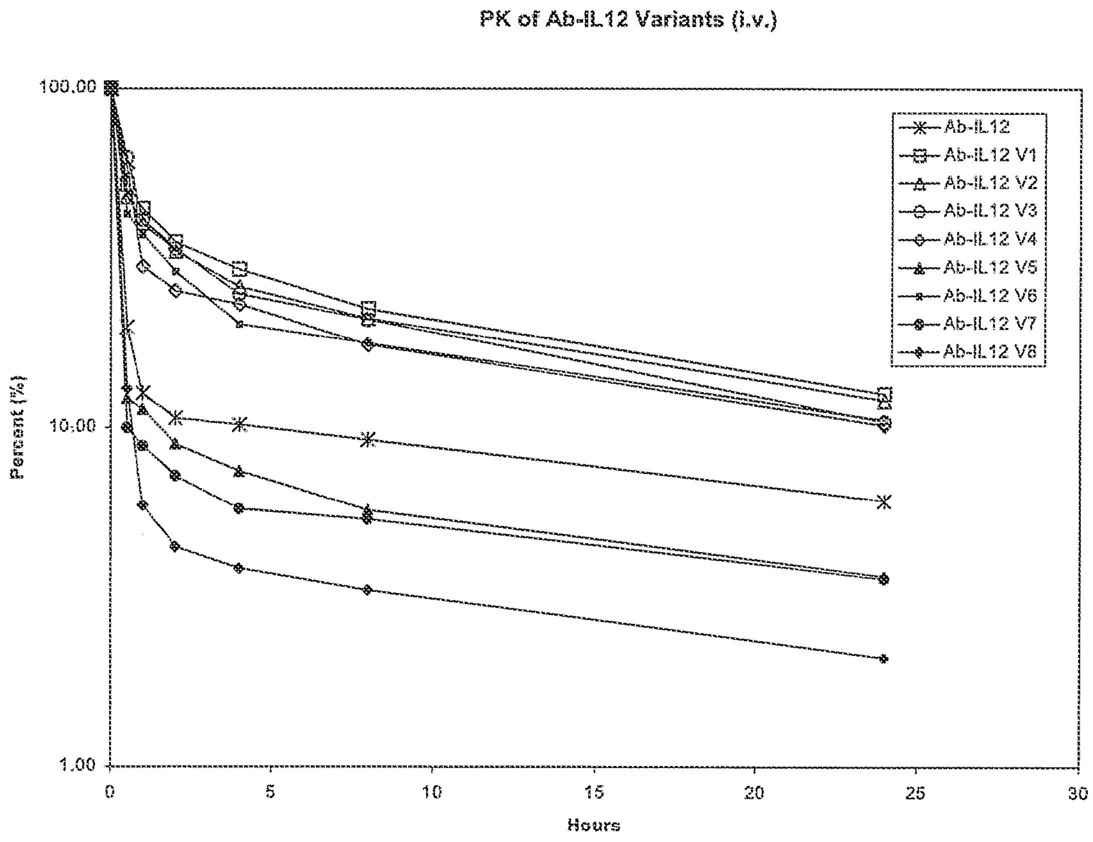
FIG. 26 shows pharmacokinetic data of antibody-IL12 fusion proteins containing p40 variants p40V1-p40V8 compared to antibody-(wild-type)-IL12 fusion proteins, administered intravenously.

FIG. 26 is a compilation of representative experiments assessing the pharmacokinetics of intravenously administered protein. It was found that compared to the wild-type control protein, antibody-IL-12 fusion proteins containing variants p40V1 and p40V2, p40V3, p40V4, as well as p40V6, had significantly improved pharmacokinetic values. Particularly, it was found that the half-life of the distribution phase (alpha phase) approximately doubled, and correspondingly the AUC of the variant proteins approximately doubled as well. However, the elimination phase (beta phase) of all Ab-IL-12 fusion proteins remained substantially similar.

Figure 27A:
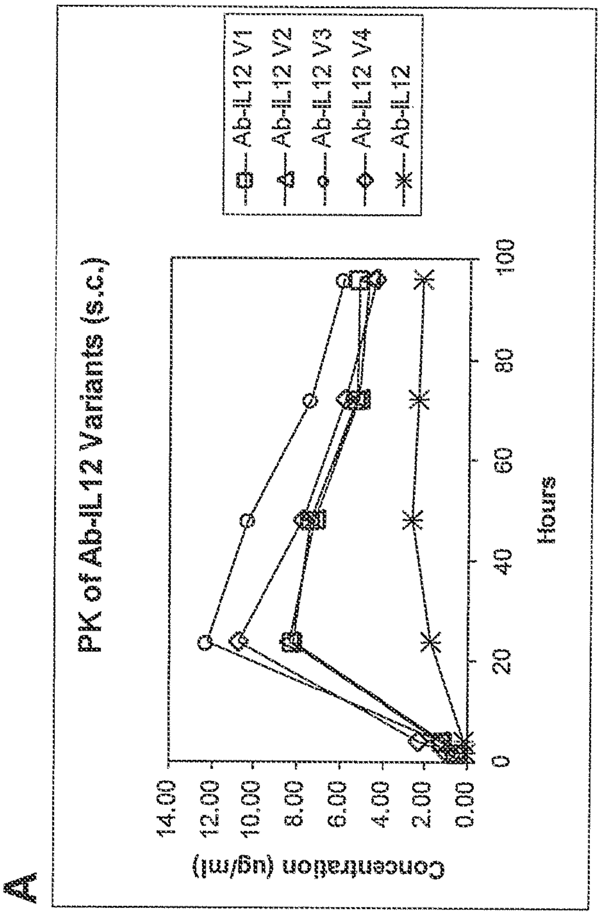
FIG. 27A shows pharmacokinetic data of antibody-IL12 fusion proteins containing p40 variants p40V1-p40V4 compared to antibody-(wild-type)-IL12 fusion proteins (panel A) and FIG. 27B shows pharmacokinetic data of antibody-IL12 fusion proteins containing p40 variants p40V5-p40V8 compared to antibody-(wild-type)-IL12 fusion proteins (panel B), administered subcutaneously.
Figure 27B:
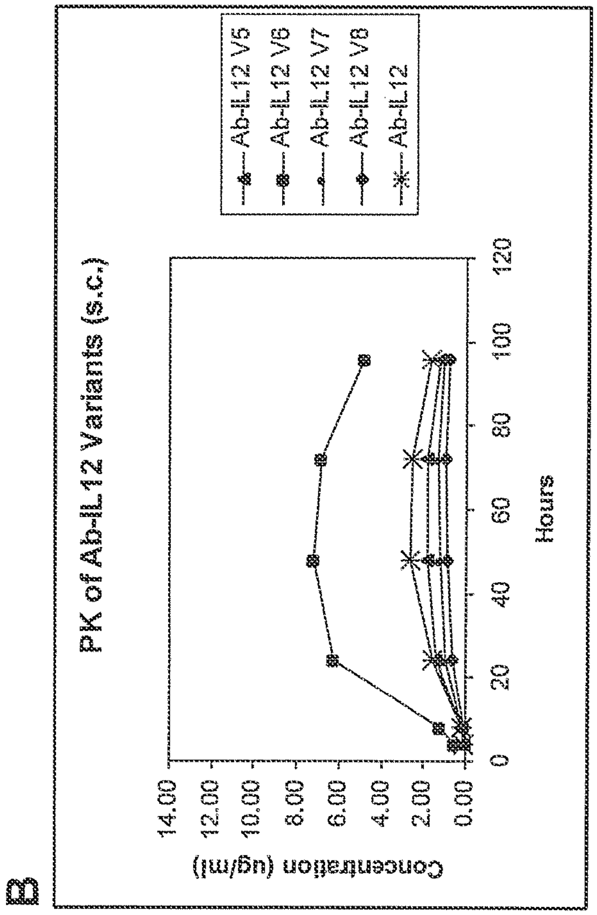

These results were consistent with the pharmacokinetics of these proteins when administered to the mouse subcutaneously FIG. 27, panel A, shows a comparison of wild-type Ab-IL12 with Ab-IL12 variants containing p40 V1, p40 V2, p40 V3, and p40 V4, and panel B shows a comparison of wild-type Ab-IL12 with Ab-IL12 variants containing p40 V5, p40 V6, p40 V7, and p40 V8.

Example 7

Treatment of a Human Patient with IL-12p40 Variants

The IL-12p40 variants of the invention are used to prevent and treat human diseases and disorders as follows. In general, the preferred method of administration is by i.v. infusion or i.v. injection, or by subcutaneous injection, inhalation, although oral delivery, and other methods are also possible.

A patient with advanced metastatic prostate cancer, with a history of treatment by conventional chemotherapy, is treated as follows with an antibody-IL12 fusion protein containing an IL-12p40 variant. The dose of the antibody-IL12 fusion protein per treatment cycle is about 150 micrograms per kg of body weight, and may be delivered on a single day or on two or three adjacent days, with administration by drip infusion. Treatment may be combined with a standard-of-care treatment for prostate cancer as determined by a physician as appropriate for the patient. Non-steroidal anti-inflammatory drugs, for example Naproxen™, are also prescribed. Treatment cycles are repeated about once every three weeks.

A patient with hormone-refractory breast cancer is treated by drip infusion with an antibody-IL12 fusion protein containing IL-12p40 variant. Non-steroidal anti-inflammatory drugs, for example Naproxen™ are also prescribed.

In an alternative treatment strategy, a patient with advanced hormone-refractory prostate cancer or advanced hormone-refractory breast cancer is treated with antibody-IL12 fusion protein containing an IL-12p40 variant about once every three weeks, in combination with an IL-2-containing immunocytokine such as KS-IL2. These two agents may be co-administered by drip infusion. Prior to the treatment, the patient is dosed with an immunostimulatory amount of cyclophosphamide. Non-steroidal anti-inflammatory drugs, for example Naproxen™ are also prescribed.

A patient with rheumatoid arthritis is treated with an Fc-p40 fusion protein, in which the p40 subunit is an IL-12p40 variant, about once every two weeks at a dose of about 8 mg/kg, with administration by drip infusion. Progression of joint destruction is found to be significantly inhibited by monotherapy, even when compared to disease-modifying anti-rheumatic drugs.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which comes within the meaning and range of equivalency of the claims are intended to be embraced therein.

What is claimed is:

1. A method of treating a patient having cancer, the method comprising the step of administering to the patient a therapeutically effective amount of a composition comprising a variant of an IL-12p40 subunit, the variant selected from the group consisting of:

(a) a variant being at least 90% identical to SEQ ID NO:2 and comprising an amino acid alteration at one or more positions corresponding to residues 258-266, wherein the amino acid alteration comprises an amino acid substitution selected from the group consisting of Lys260Asn, Lys260Gln, and Lys260Gly;

(b) a variant being at least 90% identical to SEQ ID NO:2 and comprising an amino acid alteration at one or more positions corresponding to amino acids 258-266, wherein the amino acid alteration comprises an amino acid substitution at Lys260 and deletion of one or more of Lys258, Ser259, Lys263, Lys264, and Asp265;

(c) a variant being at least 90% identical to SEQ ID NO:2 and comprising an amino acid alteration at one or more positions corresponding to amino acids 258-266, wherein the amino acid alteration comprises an amino acid substitution at Lys260 and one or more of amino acid substitutions Lys258Gln, Ser259Asp, and Lys260Gln;

(d) a variant being at least 90% identical to SEQ ID NO:2 and comprising an amino acid alteration at one or more positions corresponding to amino acids 258-266, wherein the amino acid alteration comprises the amino acid substitution Ser259Asp; and (e) a variant being at least 90% identical to SEQ ID NO:2 and comprising an amino acid alteration at one or more positions corresponding to residues 258-266, wherein the amino acid alteration comprises an amino acid substitution selected from the group consisting of Arg261Asp and Arg261Thr.

2. The method of claim 1, wherein variant (a) comprises one or more amino acid substitutions at positions selected from the group consisting of Lys258, Ser259, Arg261, Lys263, Lys264, and Arg266.

3. The method of claim 2, wherein variant (a) comprises one or more of Lys258Gln, Ser259Asp, Arg261Ala, Arg261Asp, Arg261Thr, Lys263Gly, Lys263Ser, and Lys264Gly.

4. The method of claim 1, wherein variant (a) further comprises substitutions at Ser259 and Arg261.

5. The method of claim 4, wherein variant (a) comprises the substitutions Ser259Asp, Lys260Asn, and Arg261Thr.

6. The method of claim 4, wherein one or more residues corresponding to Lys263, Lys264, Asp265, and Arg266 are deleted from variant (a).

7. The method of claim 5, wherein residues Lys263, Lys264, and Asp265 of variant (a) are deleted.

8. The method of claim 1, wherein the variant is at least 95% identical to SEQ ID NO:2.

9. The method of claim 1, wherein variant (d) further comprises a substitution at position Lys260.

10. The method of claim 9, wherein Lys260 of variant (d) is replaced with a non-basic amino acid.

11. The method of claim 10, wherein the non-basic amino acid is Ala, Asn, Gln, or Gly.

12. The method of claim 1, wherein variant (e) comprises a substitution at position Lys260.

13. The method of claim 12, wherein the Lys260 of variant (e) is replaced with a non-basic amino acid.

14. The variant of claim 13, wherein the non-basic amino acid is Ala, Asn, Gln, or Gly.

15. The method of claim 1, wherein the variant comprises a fusion protein, the fusion protein further comprising an antibody moiety or an active fragment thereof, or a non-IL-12 cytokine or an active portion thereof.

16. The method of claim 1, wherein the variant is the IL-12p40 subunit of an IL-12 polypeptide administered to the patient.

17. The method of claim 16, wherein the IL-12 polypeptide is administered in the amount of about 0.01 mg/kg/day to about 10 mg/kg/day.

18. The method of claim 16, wherein the IL-12 polypeptide comprises a fusion protein comprising an antibody moiety or an active fragment thereof, or a non-IL-12 cytokine or an active portion thereof.

19. The method of claim 18, wherein the IL-12 fusion protein comprises an antibody moiety or an active fragment thereof and the IL-12 fusion protein is administered in the amount of about 0.001 mg/kg/day to about 1 mg/kg/day.

20. The method of claim 1, wherein the variant is the IL-12p40 subunit of an IL-23 polypeptide administered to the patient.

21. The method of claim 20, wherein the IL-23 polypeptide is administered in the amount of about 0.01 mg/kg/day to about 10 mg/kg/day.

22. The method of claim 20, wherein the IL-23 polypeptide comprises a fusion protein comprising an antibody moiety or an active fragment thereof, or a non-IL-12 cytokine or an active portion thereof.

23. The method of claim 22, wherein the IL-23 fusion protein comprises an antibody moiety or an active fragment thereof and the IL-23 fusion protein is administered in the amount of about 0.001 mg/kg/day to about 1 mg/kg/day.

24. The method of claim 1, wherein the variant is administered intravenously, intradermally, subcutaneously, orally, transdermally, transmucosally, or rectally.

25. The method of claim 1, wherein the cancer is renal cancer, colon cancer, ovarian cancer, melanoma, T-cell lymphoma, prostate cancer, or breast cancer.

26. The method of claim 1, wherein the composition comprising a variant of IL-12p40 is administered as an adjuvant for treating the cancer.

* * * * *

SEQUENCE LISTING

```
<160> NUMBER OF SEQ ID NOS: 44

<210> SEQ ID NO 1
<211> LENGTH: 197
<212> TYPE: PRT
<213> ORGANISM: Homo sapiens

<400> SEQUENCE: 1

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140
```

```
Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
            195

<210> SEQ ID NO 2
<211> LENGTH: 306
<212> TYPE: PRT
<213> ORGANISM: Homo sapiens

<400> SEQUENCE: 2

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

-continued

<210> SEQ ID NO 3
<211> LENGTH: 169
<212> TYPE: PRT
<213> ORGANISM: Homo sapiens

<400> SEQUENCE: 3

```
Ala Val Pro Gly Gly Ser Ser Pro Ala Trp Thr Gln Cys Gln Gln Leu
1               5                   10                  15

Ser Gln Lys Leu Cys Thr Leu Ala Trp Ser Ala His Pro Leu Val Gly
            20                  25                  30

His Met Asp Leu Arg Glu Glu Gly Asp Glu Glu Thr Thr Asn Asp Val
        35                  40                  45

Pro His Ile Gln Cys Gly Asp Gly Cys Asp Pro Gln Gly Leu Arg Asp
    50                  55                  60

Asn Ser Gln Phe Cys Leu Gln Arg Ile His Gln Gly Leu Ile Phe Tyr
65                  70                  75                  80

Glu Lys Leu Leu Gly Ser Asp Ile Phe Thr Gly Glu Pro Ser Leu Leu
                85                  90                  95

Pro Asp Ser Pro Val Gly Gln Leu His Ala Ser Leu Leu Gly Leu Ser
            100                 105                 110

Gln Leu Leu Gln Pro Glu Gly His His Trp Glu Thr Gln Gln Ile Pro
        115                 120                 125

Ser Leu Ser Pro Ser Gln Pro Trp Gln Arg Leu Leu Leu Arg Phe Lys
    130                 135                 140

Ile Leu Arg Ser Leu Gln Ala Phe Val Ala Val Ala Ala Arg Val Phe
145                 150                 155                 160

Ala His Gly Ala Ala Thr Leu Ser Pro
                165
```

<210> SEQ ID NO 4
<211> LENGTH: 46
<212> TYPE: PRT
<213> ORGANISM: Homo sapiens

<400> SEQUENCE: 4

```
Arg Glu Lys Lys Asp Arg Val Phe Thr Asp Lys Thr Ser Ala Thr Val
1               5                   10                  15

Ile Cys Arg Lys Asn Ala Ser Ile Ser Val Arg Ala Gln Asp Arg Tyr
            20                  25                  30

Tyr Ser Ser Ser Trp Ser Glu Trp Ala Ser Val Pro Cys Ser
        35                  40                  45
```

<210> SEQ ID NO 5
<211> LENGTH: 9
<212> TYPE: PRT
<213> ORGANISM: Homo sapiens

<400> SEQUENCE: 5

```
Lys Ser Lys Arg Glu Lys Lys Asp Arg
1               5
```

<210> SEQ ID NO 6
<211> LENGTH: 303
<212> TYPE: PRT
<213> ORGANISM: Artificial Sequence
<220> FEATURE:
<223> OTHER INFORMATION: synthetic: engineered mature human IL-12p40V1
subunit -continued

<400> SEQUENCE: 6

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Asp Asn Thr Glu Arg Val Phe Thr Asp Lys Thr Ser Ala Thr
            260                 265                 270

Val Ile Cys Arg Lys Asn Ala Ser Ile Ser Val Arg Ala Gln Asp Arg
        275                 280                 285

Tyr Tyr Ser Ser Ser Trp Ser Glu Trp Ala Ser Val Pro Cys Ser
    290                 295                 300
```

<210> SEQ ID NO 7
<211> LENGTH: 304
<212> TYPE: PRT
<213> ORGANISM: Artificial Sequence
<220> FEATURE:
<223> OTHER INFORMATION: synthetic: engineered mature human IL-12p40V2 subunit

<400> SEQUENCE: 7

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45
```

```
Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Asp Asn Thr Glu Gly Arg Val Phe Thr Asp Lys Thr Ser Ala
            260                 265                 270

Thr Val Ile Cys Arg Lys Asn Ala Ser Ile Ser Val Arg Ala Gln Asp
        275                 280                 285

Arg Tyr Tyr Ser Ser Ser Trp Ser Glu Trp Ala Ser Val Pro Cys Ser
    290                 295                 300


<210> SEQ ID NO 8
<211> LENGTH: 306
<212> TYPE: PRT
<213> ORGANISM: Artificial Sequence
<220> FEATURE:
<223> OTHER INFORMATION: synthetic: engineered mature human IL-12p40V3
      subunit

<400> SEQUENCE: 8

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110
```

```
Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Gln Asp Gln Asp Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 9
<211> LENGTH: 306
<212> TYPE: PRT
<213> ORGANISM: Artificial Sequence
<220> FEATURE:
<223> OTHER INFORMATION: synthetic: engineered mature human IL-12p40V4
      subunit

<400> SEQUENCE: 9

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
```

-continued

```
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Gln Asp Gln Asp Glu Ser Gly Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 10
<211> LENGTH: 306
<212> TYPE: PRT
<213> ORGANISM: Artificial Sequence
<220> FEATURE:
<223> OTHER INFORMATION: synthetic: engineered mature human IL-12p40V5
      subunit

<400> SEQUENCE: 10

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190
```

Val His Lys Leu Lys Tyr Glu Asn Tyr Thr Ser Ser Phe Phe Ile Arg
195 200 205

Asp Ile Ile Lys Pro Asp Pro Pro Lys Asn Leu Gln Leu Lys Pro Leu
210 215 220

Lys Asn Ser Arg Gln Val Glu Val Ser Trp Glu Tyr Pro Asp Thr Trp
225 230 235 240

Ser Thr Pro His Ser Tyr Phe Ser Leu Thr Phe Cys Val Gln Val Gln
245 250 255

Gly Lys Ser Lys Ala Glu Lys Lys Asp Arg Val Phe Thr Asp Lys Thr
260 265 270

Ser Ala Thr Val Ile Cys Arg Lys Asn Ala Ser Ile Ser Val Arg Ala
275 280 285

Gln Asp Arg Tyr Tyr Ser Ser Ser Trp Ser Glu Trp Ala Ser Val Pro
290 295 300

Cys Ser
305

<210> SEQ ID NO 11
<211> LENGTH: 306
<212> TYPE: PRT
<213> ORGANISM: Artificial Sequence
<220> FEATURE:
<223> OTHER INFORMATION: synthetic: engineered mature human IL-12p40V6 subunit

<400> SEQUENCE: 11

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala
180 185 190

Val His Lys Leu Lys Tyr Glu Asn Tyr Thr Ser Ser Phe Phe Ile Arg
195 200 205

Asp Ile Ile Lys Pro Asp Pro Pro Lys Asn Leu Gln Leu Lys Pro Leu
210 215 220

Lys Asn Ser Arg Gln Val Glu Val Ser Trp Glu Tyr Pro Asp Thr Trp
225 230 235 240

```
Ser Thr Pro His Ser Tyr Phe Ser Leu Thr Phe Cys Val Gln Val Gln
                245                 250                 255

Gly Lys Ser Ala Ala Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 12
<211> LENGTH: 306
<212> TYPE: PRT
<213> ORGANISM: Artificial Sequence
<220> FEATURE:
<223> OTHER INFORMATION: synthetic: engineered mature human IL-12p40V7
      subunit

<400> SEQUENCE: 12

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Ala Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
```

```
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 13
<211> LENGTH: 306
<212> TYPE: PRT
<213> ORGANISM: Artificial Sequence
<220> FEATURE:
<223> OTHER INFORMATION: synthetic: engineered mature human IL-12p40V8
      subunit

<400> SEQUENCE: 13

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Gly Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

-continued

<210> SEQ ID NO 14
<211> LENGTH: 306
<212> TYPE: PRT
<213> ORGANISM: Artificial Sequence
<220> FEATURE:
<223> OTHER INFORMATION: synthetic: engineered mature human IL-12p40V9
subunit

<400> SEQUENCE: 14

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Gln Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 15
<211> LENGTH: 306
<212> TYPE: PRT
<213> ORGANISM: Artificial Sequence
<220> FEATURE:
<223> OTHER INFORMATION: synthetic: engineered mature human IL-12p40V10
subunit -continued

<400> SEQUENCE: 15

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asp Pro Gln
130 135 140

Gly Val Thr Cys Gly Ala Ala Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Ser Leu Pro Ile Glu Val Met Val Asp Ala
180 185 190

Val His Lys Leu Lys Tyr Glu Asn Tyr Thr Ser Ser Phe Phe Ile Arg
195 200 205

Asp Ile Ile Lys Pro Asp Pro Pro Lys Asn Leu Gln Leu Lys Pro Leu
210 215 220

Lys Asn Ser Arg Gln Val Glu Val Ser Trp Glu Tyr Pro Asp Thr Trp
225 230 235 240

Ser Thr Pro His Ser Tyr Phe Ser Leu Thr Phe Cys Val Gln Val Gln
245 250 255

Gly Lys Ser Lys Asp Glu Lys Lys Asp Arg Val Phe Thr Asp Lys Thr
260 265 270

Ser Ala Thr Val Ile Cys Arg Lys Asn Ala Ser Ile Ser Val Arg Ala
275 280 285

Gln Asp Arg Tyr Tyr Ser Ser Ser Trp Ser Glu Trp Ala Ser Val Pro
290 295 300

Cys Ser
305

<210> SEQ ID NO 16
<211> LENGTH: 306
<212> TYPE: PRT
<213> ORGANISM: Artificial Sequence
<220> FEATURE:
<223> OTHER INFORMATION: synthetic: engineered mature human IL-12p40v11
subunit

<400> SEQUENCE: 16

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

-continued

```
Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Gln Asp Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 17
<211> LENGTH: 6
<212> TYPE: PRT
<213> ORGANISM: Artificial Sequence
<220> FEATURE:
<223> OTHER INFORMATION: synthetic: fragment of engineered mature human
      IL-12p40V1 subunit

<400> SEQUENCE: 17

Lys Asp Asn Thr Glu Arg
1               5


<210> SEQ ID NO 18
<211> LENGTH: 7
<212> TYPE: PRT
<213> ORGANISM: Artificial Sequence
<220> FEATURE:
<223> OTHER INFORMATION: synthetic: fragment of engineered mature human
      IL-12p40V2 subunit

<400> SEQUENCE: 18
```

Lys Asp Asn Thr Glu Gly Arg
1 5

<210> SEQ ID NO 19
<211> LENGTH: 9
<212> TYPE: PRT
<213> ORGANISM: Artificial Sequence
<220> FEATURE:
<223> OTHER INFORMATION: synthetic: fragment of engineered mature human IL-12p40V3 subunit

<400> SEQUENCE: 19

Gln Asp Gln Asp Glu Lys Lys Asp Arg
1 5

<210> SEQ ID NO 20
<211> LENGTH: 9
<212> TYPE: PRT
<213> ORGANISM: Artificial Sequence
<220> FEATURE:
<223> OTHER INFORMATION: synthetic: fragment of engineered mature human IL-12p40V4 subunit

<400> SEQUENCE: 20

Gln Asp Gln Asp Glu Ser Gly Asp Arg
1 5

<210> SEQ ID NO 21
<211> LENGTH: 987
<212> TYPE: DNA
<213> ORGANISM: Homo sapiens

<400> SEQUENCE: 21
atgtgtcacc agcagttggt catctcttgg ttttccctgg tttttctggc atctcccctc 60
gtggccatat gggaactgaa gaaagatgtt tatgtcgtag aattggattg gtatccggat 120
gcccctggag aaatggtggt cctcacctgt gacacccctg aagaagatgg tatcacctgg 180
accttggacc agagcagtga ggtcttaggc tctggcaaaa ccctgaccat ccaagtcaaa 240
gagtttggag atgctggcca gtacacctgt cacaaaggag gcgaggttct aagccattcg 300
ctcctgctgc ttcacaaaaa ggaagatgga atttggtcca ctgatatttt aaaggaccag 360
aaagaaccca aaaataagac ctttctaaga tgcgaggcca agaattattc tggacgtttc 420
acctgctggt ggctgacgac aatcagtact gatttgacat tcagtgtcaa aagcagcaga 480
ggctcttctg acccccaagg ggtgacgtgc ggagctgcta cactctctgc agagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gaaaactaca ccagcagctt cttcatcagg gacatcatca aacctgaccc acccaagaac 720
ttgcagctga agccattaaa gaattctcgg caggtggagg tcagctggga gtaccctgac 780
acctggagta ctccacattc ctacttctcc ctgacattct gcgttcaggt ccagggcaag 840
agcaagagag aaaagaaaga tagagtcttc acggacaaga cctcagccac ggtcatctgc 900
cgcaaaaatg ccagcattag cgtgcgggcc caggaccgct actatagctc atcttggagc 960
gaatgggcat ctgtgccctg cagttag 987

<210> SEQ ID NO 22
<211> LENGTH: 300
<212> TYPE: DNA
<213> ORGANISM: Artificial Sequence -continued

```
<220> FEATURE:
<223> OTHER INFORMATION: synthetic: nucleic acid encoding the protein of
      SEQ ID NO:17, a linker, and the protein of SEQ ID NO:18

<400> SEQUENCE: 22

gaattctcgg caggtggagg tcagctggga gtaccctgac acctggagca ctccacattc     60

ctacttctcc ctgacattct gcgttcaggt ccagggcaag gacaatacgg agagagtgtt    120

cacggacaag acctcagctt ttttttttt ttgaagactc aattctcggc aggtggaggt    180

cagctgggag taccctgaca cctggagtac tccacattcc tacttctccc tgacattctg    240

cgttcaggtc cagggcaagg acaatacgga gggtagagtg ttcacggaca agacctcagc    300


<210> SEQ ID NO 23
<211> LENGTH: 277
<212> TYPE: DNA
<213> ORGANISM: Artificial Sequence
<220> FEATURE:
<223> OTHER INFORMATION: synthetic: nucleic acid encoding the protein of
      SEQ ID NO:19, a linker, and the protein of SEQ ID NO:20

<400> SEQUENCE: 23

gaattctcgg caggtggagg tcagctggga gtaccctgac acctggagca ctccacattc     60

ctacttctcc ctgacattct gcgttcaggt ccagggccag gatcaggacg agaagaagga    120

tagagtcttc ttttttttt gaagactcaa ttctcggcag gtggaggtca gctgggagta    180

ccctgacacc tggagtactc cacattccta cttctccctg acattctgcg ttcaggtcca    240

gggccaggat caggacgagt ccggagatag agtcttc                             277


<210> SEQ ID NO 24
<211> LENGTH: 312
<212> TYPE: DNA
<213> ORGANISM: Artificial Sequence
<220> FEATURE:
<223> OTHER INFORMATION: synthetic: nucleic acid encoding a fragment of
      IL-12p40V5, a linker, and a fragment of IL-12p40V6

<400> SEQUENCE: 24

gaattctcgg caggtggagg tcagttggga gtaccctgac acctggagca ctccacattc     60

ctacttctcc ctgacattct gcgttcaggt ccagggcaag agcaaggcag aaaagaaaga    120

tagagtcttc acggacaaga cctcagcttt tttttttga agactcaatt ctcggcaggt    180

ggaggtcagt tgggagtacc ctgacacctg gagtactcca cattcctact tctccctgac    240

attctgcgtt caggtccagg gcaagagcgc agctgaaaag aaagatagag tctttacgga    300

caagacctca gc                                                        312


<210> SEQ ID NO 25
<211> LENGTH: 312
<212> TYPE: DNA
<213> ORGANISM: Artificial Sequence
<220> FEATURE:
<223> OTHER INFORMATION: synthetic: nucleic acid encoding a fragment of
      IL-12p40V7, a linker, and a fragment of IL-12p40V8

<400> SEQUENCE: 25

gaattctcgg caggtggagg tcagttggga gtaccctgac acctggagca ctccacattc     60

ctacttctcc ctgacattct gcgttcaggt ccagggcaag agcgcccggg aaaagaaaga    120

tagagtcttc acggacaaga cctcagcttt tttttttga agactcaatt ctcggcaggt    180

ggaggtcagt tgggagtacc ctgacacctg gagtactcca cattcctact tctccctgac    240
```

attctgcgtt caggtccagg gcaagagcgg tagagaaaag aaagatagag tctttacgga 300
caagacctca gc 312

<210> SEQ ID NO 26
<211> LENGTH: 96
<212> TYPE: PRT
<213> ORGANISM: Homo sapiens

<400> SEQUENCE: 26

Ile Lys Pro Asp Pro Pro Lys Asn Leu Gln Leu Lys Pro Leu Lys Asn
1 5 10 15

Ser Arg Gln Val Glu Val Ser Trp Glu Tyr Pro Asp Thr Trp Ser Thr
20 25 30

Pro His Ser Tyr Phe Ser Leu Thr Phe Cys Val Gln Val Gln Gly Lys
35 40 45

Ser Lys Arg Glu Lys Lys Asp Arg Val Phe Thr Asp Lys Thr Ser Ala
50 55 60

Thr Val Ile Cys Arg Lys Asn Ala Ser Ile Ser Val Arg Ala Gln Asp
65 70 75 80

Arg Tyr Tyr Ser Ser Ser Trp Ser Glu Trp Ala Ser Val Pro Cys Ser
85 90 95

<210> SEQ ID NO 27
<211> LENGTH: 306
<212> TYPE: PRT
<213> ORGANISM: Papio anubis

<400> SEQUENCE: 27

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Gly Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Ala Leu Ser His Ser Leu Leu
65 70 75 80

Leu Leu His Lys Lys Glu Asp Gly Ile Trp Ser Thr Asp Val Leu Lys
85 90 95

Asp Gln Lys Glu Pro Lys Asn Lys Thr Phe Leu Arg Cys Glu Ala Lys
100 105 110

Asn Tyr Ser Gly Arg Phe Thr Cys Trp Trp Leu Thr Thr Ile Ser Thr
115 120 125

Asp Leu Thr Phe Ser Val Lys Ser Ser Arg Gly Ser Ser Asn Pro Gln
130 135 140

Gly Val Thr Cys Gly Ala Val Thr Leu Ser Ala Glu Arg Val Arg Gly
145 150 155 160

Asp Asn Lys Glu Tyr Glu Tyr Ser Val Glu Cys Gln Glu Asp Ser Ala
165 170 175

Cys Pro Ala Ala Glu Glu Arg Leu Pro Ile Glu Val Met Val Asp Ala
180 185 190

Ile His Lys Leu Lys Tyr Glu Asn Tyr Thr Ser Ser Phe Phe Ile Arg
195 200 205

Asp Ile Ile Lys Pro Asp Pro Pro Lys Asn Leu Gln Leu Lys Pro Leu
210 215 220

-continued

```
Lys Asn Ser Arg Gln Ala Glu Val Ser Trp Glu Tyr Pro Asp Thr Trp
225                 230                 235                 240

Ser Thr Pro His Ser Tyr Phe Ser Leu Thr Phe Cys Ile Gln Val Gln
                245                 250                 255

Gly Lys Ser Lys Arg Glu Lys Lys Asp Arg Ile Phe Thr Asp Lys Thr
            260                 265                 270

Ser Ala Thr Val Ile Cys Arg Lys Asn Ala Ser Phe Ser Val Gln Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 28
<211> LENGTH: 306
<212> TYPE: PRT
<213> ORGANISM: Macaca mulatta

<400> SEQUENCE: 28

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Gly Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Ala Leu Ser His Ser Leu Leu
65                  70                  75                  80

Leu Leu His Lys Lys Glu Asp Gly Ile Trp Ser Thr Asp Val Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asn Pro Gln
    130                 135                 140

Gly Val Thr Cys Gly Ala Val Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Arg Leu Pro Ile Glu Val Met Val Asp Ala
            180                 185                 190

Ile His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Ile Gln Val Gln
                245                 250                 255

Gly Lys Ser Lys Arg Glu Lys Lys Asp Arg Ile Phe Thr Asp Lys Thr
            260                 265                 270

Ser Ala Thr Val Ile Cys Arg Lys Asn Ala Ser Phe Ser Val Gln Ala
```

```
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 29
<211> LENGTH: 306
<212> TYPE: PRT
<213> ORGANISM: Cercocebus torquatos

<400> SEQUENCE: 29

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Gly Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Ala Leu Ser His Ser Leu Leu
65                  70                  75                  80

Leu Pro His Lys Lys Glu Asp Gly Ile Trp Ser Thr Asp Ile Leu Lys
                85                  90                  95

Asp Gln Lys Glu Pro Lys Asn Glu Thr Phe Leu Arg Cys Glu Ala Lys
            100                 105                 110

Asn Tyr Ser Gly Arg Ile Thr Cys Trp Trp Leu Ser Thr Ile Ser Thr
        115                 120                 125

Asp Leu Thr Phe Ser Ile Ile Ser Ser Arg Gly Ser Ser Asn Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Arg Leu Pro Ile Glu Val Met Val Asp Ala
            180                 185                 190

Ile His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Ile Gln Val Gln
                245                 250                 255

Gly Lys Ser Lys Arg Glu Lys Lys Asp Arg Ile Phe Thr Asp Lys Thr
            260                 265                 270

Ser Ala Thr Val Ile Cys Arg Lys Asn Ala Ser Phe Ser Val Gln Ala
        275                 280                 285

Gln Asp Arg Tyr Tyr Ser Ser Ser Trp Asn Glu Trp Thr Ser Val Pro
    290                 295                 300

Cys Ser
305


<210> SEQ ID NO 30
<211> LENGTH: 307
```

<212> TYPE: PRT
<213> ORGANISM: Canis familiaris

<400> SEQUENCE: 30

Ile Trp Glu Leu Glu Lys Asp Val Tyr Val Val Glu Leu Asp Trp His
1               5                   10                  15

Pro Asp Ala Pro Gly Glu Met Val Val Leu Thr Cys His Thr Pro Glu
            20                  25                  30

Glu Asp Asp Ile Thr Trp Thr Ser Ala Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
                165                 170                 175

Ala Cys Pro Ser Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Thr Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Val Gln Ala
                245                 250                 255

Gln Gly Lys Asn Asn Arg Glu Lys Lys Asp Arg Leu Cys Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asp Trp Ala Ser Val
    290                 295                 300

Ser Cys Ser
305

<210> SEQ ID NO 31
<211> LENGTH: 307
<212> TYPE: PRT
<213> ORGANISM: Felis catus

<400> SEQUENCE: 31

Ile Trp Glu Leu Glu Lys Asn Val Tyr Val Val Glu Leu Asp Trp His
1               5                   10                  15

Pro Asp Ala Pro Gly Glu Met Val Val Leu Thr Cys Asp Thr Pro Glu
            20                  25                  30

```
Glu Asp Asp Ile Thr Trp Thr Ser Asp Gln Ser Ser Glu Val Leu Gly
        35                  40                  45

Ser Gly Lys Thr Leu Thr Ile Gln Val Lys Glu Phe Ala Asp Ala Gly
    50                  55                  60

Gln Tyr Thr Cys His Lys Gly Gly Glu Val Leu Ser His Ser Phe Leu
65                  70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Thr Val Lys Ser Ser Arg Gly Ser Ser Asp Pro Gln
    130                 135                 140

Gly Val Thr Cys Gly Ala Ala Thr Leu Ser Ala Glu Lys Val Arg Val
145                 150                 155                 160

Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
    290                 295                 300

Ser Cys Ser
305


<210> SEQ ID NO 32
<211> LENGTH: 307
<212> TYPE: PRT
<213> ORGANISM: Equus caballus

<400> SEQUENCE: 32

Ile Trp Glu Leu Glu Lys Asp Val Tyr Val Val Glu Leu Asp Trp Tyr
1               5                   10                  15

Pro Asp Ala Pro Gly Glu Met Val Val Leu Thr Cys Asn Thr Pro Glu
            20                  25                  30

Glu Glu Gly Ile Thr Trp Thr Ser Ala Gln Ser Asn Glu Val Leu Gly
        35                  40                  45

Ser Gly Lys Thr Leu Thr Ile Gln Val Lys Glu Phe Gly Asp Ala Gly
    50                  55                  60

Trp Tyr Thr Cys His Lys Gly Gly Glu Val Leu Ser His Ser His Leu
65                  70                  75                  80

Leu Leu His Lys Lys Glu Asp Gly Ile Trp Ser Thr Asp Ile Leu Lys
                85                  90                  95
```

```
Asp Gln Lys Glu Ser Lys Asn Lys Thr Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Ser Asp Pro Arg
    130                 135                 140

Gly Val Thr Cys Gly Ala Ala Thr Leu Ser Ala Glu Arg Val Ser Val
145                 150                 155                 160

Asp Asp Arg Glu Tyr Lys Lys Tyr Thr Val Glu Cys Gln Glu Gly Ser
                165                 170                 175

Ala Cys Pro Ala Ala Glu Glu Ser Leu Pro Ile Glu Ile Val Val Asp
            180                 185                 190

Ala Val His Lys Leu Lys Tyr Glu Asn Tyr Thr Ser Gly Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg Gln Val Glu Val Ser Trp Glu Tyr Pro Glu Thr
225                 230                 235                 240

Trp Ser Thr Pro His Ser Tyr Phe Ser Leu Thr Phe Ser Ile Gln Val
                245                 250                 255

Gln Gly Lys Asn Lys Lys Glu Arg Lys Asp Arg Leu Phe Met Asp Glu
            260                 265                 270

Thr Ser Ala Thr Val Thr Cys His Lys Asp Gly Gln Ile Arg Val Gln
        275                 280                 285

Ala Arg Asp Arg Tyr Tyr Ser Ser Ser Trp Ser Glu Trp Ala Ser Val
    290                 295                 300

Ser Cys Ser
305


<210> SEQ ID NO 33
<211> LENGTH: 302
<212> TYPE: PRT
<213> ORGANISM: Sus scrofa

<400> SEQUENCE: 33

Ile Trp Glu Leu Glu Lys Asn Val Tyr Val Val Glu Leu Asp Trp Tyr
1               5                   10                  15

Pro Asn Ala Pro Gly Glu Met Val Val Leu Thr Cys Asn Thr Pro Glu
            20                  25                  30

Glu Asp Gly Ile Thr Trp Thr Ser Asp Gln Ser Ser Glu Val Leu Gly
        35                  40                  45

Thr Gly Lys Thr Leu Thr Ile His Val Lys Glu Phe Gly Asp Ala Gly
    50                  55                  60

Gln Tyr Thr Cys Arg Lys Gly Gly Ala Val Leu Ser Gln Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Ser Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Ser Thr Asp Pro Arg
    130                 135                 140

Gly Val Thr Cys Gly Thr Ala Thr Leu Ser Glu Asp Leu Gly Glu Tyr
```

```
145                 150                 155                 160

Lys Lys Tyr Arg Val Glu Cys Gln Glu Gly Ser Ala Cys Pro Ala Ala
                165                 170                 175

Glu Glu Ser Leu Pro Ile Glu Val Val Leu Glu Ala Val His Lys Leu
            180                 185                 190

Lys Tyr Glu Asn Tyr Thr Ser Ser Phe Phe Ile Arg Asp Ile Ile Lys
        195                 200                 205

Pro Asp Pro Pro Lys Asn Leu Gln Leu Asn Pro Leu Lys Asn Ser Arg
    210                 215                 220

His Val Glu Ile Ser Trp Glu Tyr Pro Asp Thr Trp Ser Thr Pro His
225                 230                 235                 240

Ser Tyr Phe Ser Leu Met Phe Gly Val Gln Val Gln Gly Lys Asn Lys
                245                 250                 255

Arg Glu Lys Lys Asp Lys Leu Phe Thr Asp Gln Ile Ser Ala Lys Val
            260                 265                 270

Thr Cys His Lys Asp Ala Asn Ile Arg Val Gln Ala Arg Asp Arg Tyr
        275                 280                 285

Tyr Ser Ser Ser Trp Ser Glu Trp Ala Ser Val Ser Cys Asn
    290                 295                 300


<210> SEQ ID NO 34
<211> LENGTH: 305
<212> TYPE: PRT
<213> ORGANISM: Bos taurus

<400> SEQUENCE: 34

Met Trp Glu Leu Glu Lys Asn Val Tyr Val Val Glu Leu Asp Trp Tyr
1               5                   10                  15

Pro Asp Ala Pro Gly Glu Thr Val Val Leu Thr Cys Asp Thr Pro Glu
            20                  25                  30

Glu Asp Gly Ile Thr Trp Thr Ser Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Ala Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Ala Lys Ser Phe Leu Lys Cys Glu Ala Lys
            100                 105                 110

Asp Tyr Ser Gly His Phe Thr Cys Trp Trp Leu Thr Ala Ile Ser Thr
        115                 120                 125

Asp Leu Lys Phe Ser Val Lys Ser Ser Arg Gly Ser Ser Asp Pro Arg
    130                 135                 140

Gly Val Thr Cys Gly Ala Ala Leu Leu Ser Ala Glu Lys Val Ser Leu
145                 150                 155                 160

Glu His Arg Glu Tyr Asn Lys Tyr Thr Val Glu Cys Gln Glu Gly Ser
                165                 170                 175

Ala Cys Pro Ala Ala Glu Glu Ser Leu Leu Ile Glu Val Val Val Glu
            180                 185                 190

Ala Val His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Arg Pro
    210                 215                 220
```

-continued

```
Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Asn Lys Arg Glu Lys Lys Leu Phe Met Asp Gln Thr Ser
            260                 265                 270

Ala Lys Val Thr Cys His Lys Asp Ala Asn Val Arg Val Gln Ala Arg
        275                 280                 285

Asp Arg Tyr Tyr Ser Ser Phe Trp Ser Glu Trp Ala Ser Val Ser Cys
    290                 295                 300

Ser
305


<210> SEQ ID NO 35
<211> LENGTH: 305
<212> TYPE: PRT
<213> ORGANISM: Bubalus bubalis

<400> SEQUENCE: 35

Ile Trp Glu Leu Glu Lys Asn Val Tyr Ile Val Glu Leu Asp Trp Tyr
1               5                   10                  15

Pro Asp Ala Pro Gly Glu Thr Val Val Leu Thr Cys Asp Thr Pro Glu
            20                  25                  30

Glu Asp Gly Ile Thr Trp Thr Ser Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Ala Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Ala Lys Ser Phe Leu Lys Cys Glu Ala Lys
            100                 105                 110

Asp Tyr Ser Gly His Phe Thr Cys Trp Trp Leu Thr Ala Ile Ser Thr
        115                 120                 125

Asp Leu Lys Phe Ser Val Lys Ser Ser Arg Gly Ser Ala Asp Pro Arg
    130                 135                 140

Gly Val Thr Cys Gly Ala Ala Ser Leu Ser Ala Glu Lys Val Ser Val
145                 150                 155                 160

Asp His Arg Glu Tyr Asn Lys Tyr Thr Val Glu Cys Gln Glu Gly Ser
                165                 170                 175

Thr Cys Pro Ala Ala Glu Glu Ser Leu Leu Ile Glu Val Val Val Glu
            180                 185                 190

Ala Val His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Lys Pro
    210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Asn Lys Arg Glu Lys Lys Leu Phe Met Asp Gln Thr Ser
            260                 265                 270

Ala Lys Val Thr Cys His Lys Asp Ala Asn Val Arg Val Gln Ala Arg
        275                 280                 285
```

Asp Arg Tyr Tyr Ser Ser Phe Trp Ser Glu Trp Ala Ser Val Ser Cys
    290                 295                 300

Ser
305

<210> SEQ ID NO 36
<211> LENGTH: 305
<212> TYPE: PRT
<213> ORGANISM: Capra hircus

<400> SEQUENCE: 36

Ile Trp Glu Leu Glu Lys Asn Val Tyr Val Val Glu Leu Asp Trp Tyr
1               5                   10                  15

Pro Asn Ala Pro Gly Glu Thr Val Val Leu Thr Cys Asp Thr Pro Glu
            20                  25                  30

Glu Asp Gly Ile Thr Trp Thr Ser Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Ala Lys Ser Phe Leu Lys Cys Glu Ala Lys
            100                 105                 110

Asp Tyr Ser Gly His Phe Thr Cys Ser Trp Leu Thr Ala Ile Ser Thr
        115                 120                 125

Asn Leu Lys Phe Ser Val Lys Ser Ser Arg Gly Ser Ser Asp Pro Arg
    130                 135                 140

Gly Val Thr Cys Gly Ala Ala Ser Leu Ser Ala Glu Lys Val Ser Met
145                 150                 155                 160

Asp His Arg Glu Tyr Asn Lys Tyr Thr Val Glu Cys Gln Glu Gly Ser
                165                 170                 175

Ala Cys Pro Ala Ala Glu Glu Ser Leu Pro Ile Glu Val Val Met Glu
            180                 185                 190

Ala Val His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Arg Pro
    210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Asn Lys Arg Glu Lys Lys Leu Phe Thr Asp Gln Thr Ser
            260                 265                 270

Ala Lys Val Thr Cys His Lys Asp Ala Asn Ile Arg Val Gln Ala Arg
        275                 280                 285

Asp Arg Tyr Tyr Ser Ser Phe Trp Ser Glu Trp Ala Ser Val Ser Cys
    290                 295                 300

Ser
305

<210> SEQ ID NO 37
<211> LENGTH: 305
<212> TYPE: PRT

<213> ORGANISM: Ovis aries

<400> SEQUENCE: 37

```
Ile Trp Glu Leu Glu Lys Asn Val Tyr Val Val Glu Leu Asp Trp Tyr
1               5                   10                  15

Pro Asn Ala Pro Gly Glu Thr Val Val Leu Thr Cys Asp Thr Pro Glu
            20                  25                  30

Glu Asp Gly Ile Thr Trp Thr Ser Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Ala Lys Ser Phe Leu Lys Cys Glu Ala Lys
            100                 105                 110

Asp Tyr Ser Gly His Phe Thr Cys Ser Trp Leu Thr Ala Ile Ser Thr
        115                 120                 125

Asn Leu Lys Phe Ser Val Lys Ser Ser Arg Gly Ser Ser Asp Pro Arg
    130                 135                 140

Gly Val Thr Cys Gly Ala Ala Ser Leu Ser Ala Glu Lys Val Ser Met
145                 150                 155                 160

Asp His Arg Glu Tyr Asn Lys Tyr Thr Val Glu Cys Gln Glu Gly Ser
                165                 170                 175

Ala Cys Pro Ala Ala Glu Glu Ser Leu Pro Ile Glu Val Val Met Glu
            180                 185                 190

Ala Val His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Arg Pro
    210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Asn Lys Arg Glu Lys Lys Leu Phe Ala Asp Gln Thr Ser
            260                 265                 270

Ala Lys Val Thr Cys His Lys Asp Ala Asn Ile Arg Val Gln Ala Arg
        275                 280                 285

Asp Arg Tyr Tyr Ser Ser Phe Trp Ser Glu Trp Ala Ser Val Ser Cys
    290                 295                 300

Ser
305
```

<210> SEQ ID NO 38
<211> LENGTH: 305
<212> TYPE: PRT
<213> ORGANISM: Cervus elaphus

<400> SEQUENCE: 38

```
Ile Trp Glu Leu Glu Lys Asn Val Tyr Val Val Glu Leu Asp Trp Tyr
1               5                   10                  15

Pro Asp Ala Pro Gly Glu Thr Val Val Leu Arg Cys Asp Thr Pro Glu
            20                  25                  30

Glu Asp Gly Ile Thr Trp Thr Ser Asp Gln Ser Ser Glu Val Leu Gly
```

-continued

```
        35                  40                  45

Ser Gly Lys Thr Leu Thr Val Gln Val Lys Glu Phe Gly Asp Ala Gly
    50                  55                  60

Gln Tyr Thr Cys His Lys Gly Gly Glu Val Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Ala Lys Ser Phe Leu Lys Cys Glu Ala Lys
            100                 105                 110

Asp Tyr Ser Gly His Phe Thr Cys Trp Trp Leu Thr Ala Ile Ser Thr
        115                 120                 125

Asp Leu Lys Phe Ser Val Lys Ser Ser Arg Gly Ser Ser Asp Pro Arg
    130                 135                 140

Gly Val Thr Cys Gly Ala Ala Ser Leu Ser Thr Glu Lys Val Ile Val
145                 150                 155                 160

Asp His Arg Glu Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Glu
            180                 185                 190

Ala Val His Lys Leu Lys Tyr Glu Asn Tyr Thr Ser Ser Phe Phe Ile
        195                 200                 205

Arg Asp Ile Ile Lys Pro Asp Pro Pro Lys Asn Leu Gln Leu Arg Pro
    210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Asn Lys Arg Glu Lys Lys Leu Phe Met Asp Gln Thr Ser
            260                 265                 270

Ala Lys Val Thr Cys His Lys Asp Ala Ser Ile Arg Val Gln Ala Arg
        275                 280                 285

Asp Arg Tyr Tyr Asn Ser Phe Trp Ser Glu Trp Ala Ser Val Ser Cys
    290                 295                 300

Ser
305


<210> SEQ ID NO 39
<211> LENGTH: 305
<212> TYPE: PRT
<213> ORGANISM: Mesocricetus auratus

<400> SEQUENCE: 39

Ile Trp Glu Leu Glu Lys Asp Val Tyr Val Val Glu Val Asp Trp Ser
1               5                   10                  15

Pro Asp Ala Ala Gly Glu Arg Val Val Leu Thr Cys Asp Thr Ser Glu
            20                  25                  30

Glu Asp Asp Ile Ile Trp Thr Ser Asp Lys Asn Ser Glu Ala Val Gly
        35                  40                  45

Ser Gly Lys Thr Leu Thr Ile Gln Val Lys Glu Phe Ser Asn Ala Gly
    50                  55                  60

Gln Tyr Thr Cys His Lys Gly Gly Lys Thr Leu Ser His Ser Arg Leu
65                  70                  75                  80

Leu Leu His Lys Lys Glu Asn Gly Ile Trp Ser Thr Asp Ile Leu Lys
                85                  90                  95
```

```
Asp Gln Lys Asp Pro Lys Asn Lys Thr Phe Leu Lys Cys Glu Ala Ala
            100                 105                 110

Asn Tyr Ser Gly Arg Phe Thr Cys Trp Trp Leu Thr Ala Ile Ser Thr
        115                 120                 125

Asp Leu Lys Phe Asn Val Lys Ser Ser Ser Ser Ser Ser Asp Ser Arg
    130                 135                 140

Ala Val Thr Cys Gly Ala Ala Ser Leu Ser Ala Glu Lys Val Thr Val
145                 150                 155                 160

Asp Arg Lys Asp Tyr Gln Lys Tyr Ser Val Ala Cys Gln Glu Asp Ile
                165                 170                 175

Thr Cys Pro Thr Ala Glu Glu Thr Leu Pro Ile Gly Leu Val Met Glu
            180                 185                 190

Ala Gln His Lys Tyr Lys Tyr Glu Asn Tyr Ser Thr Gly Phe Phe Ile
        195                 200                 205

Arg Asp Ile Ile Lys Pro Asp Pro Pro Lys Asn Leu Gln Leu Lys Pro
    210                 215                 220

Leu Arg Gly Ser Gln Met Glu Leu Ser Trp Glu Tyr Pro Asp Ser Trp
225                 230                 235                 240

Ser Thr Pro His Ser Tyr Phe Ser Leu Lys Phe His Val Gln Val His
                245                 250                 255

Arg Lys Arg Glu Arg Lys Asp Glu Ser Gln Phe Val Asp Lys Thr Ser
            260                 265                 270

Ala Thr Ile Arg Cys Ser Lys Gly Ala Glu Val Arg Val Arg Ala Gln
        275                 280                 285

Asp His Tyr Tyr Asn Ser Ser Trp Ser Arg Trp Val Ser Val Pro Cys
    290                 295                 300

Ser
305


<210> SEQ ID NO 40
<211> LENGTH: 310
<212> TYPE: PRT
<213> ORGANISM: Cavia porcellus

<400> SEQUENCE: 40

Met Trp Glu Leu Lys Lys Asp Val Tyr Val Val Glu Leu Asp Trp His
1               5                   10                  15

Thr Asp Ala Pro Gly Glu Thr Val Val Leu Thr Cys Asn Thr Ala Glu
            20                  25                  30

Glu Asp Gly Ile Thr Trp Thr Ser Asp Arg Lys Ser Asp Ile Leu Gly
        35                  40                  45

Ser Gly Lys Thr Leu Thr Ile Gln Val Lys Glu Phe Glu Asp Ala Gly
    50                  55                  60

Gly Tyr Thr Cys His Lys Gly Gly Glu Val Leu Ser Arg Ser Gln Leu
65                  70                  75                  80

Leu Leu His Lys Lys Glu Asp Glu Ile Trp Ser Thr Asp Ile Leu Lys
                85                  90                  95

Glu Gln Lys Gly Ser Asn Gly Lys Thr Phe Leu Lys Cys Glu Ala Arg
            100                 105                 110

Ser Tyr Ser Gly Arg Phe Thr Cys Trp Trp Leu Thr Ala Phe Gly Thr
        115                 120                 125

Asp Val Lys Phe Ser Val Lys Gly Ser Arg Gly Ser Ser Asp Pro Ser
    130                 135                 140

Gly Val Thr Cys Gly Glu Ala Glu Arg Val Ser Gly Asp Asn Gln Glu
145                 150                 155                 160
```

```
Tyr Lys Tyr Ser Val Glu Cys Gln Glu Asp Ser Ala Cys Pro Thr Ala
                165                 170                 175

Glu Glu Ser Leu Pro Ile Glu Val Val Val Asp Ala Ile His Lys Phe
            180                 185                 190

Lys Tyr Glu Asn Tyr Thr Ser Ser Phe Tyr Ile Arg Asp Ile Ile Lys
        195                 200                 205

Pro Asp Pro Pro Lys Asn Leu Gln Leu Lys Pro Ser Val Asn Ser Gln
    210                 215                 220

Gln Val Glu Val Ser Trp Glu Tyr Pro Asp Thr Trp Ser Thr Pro His
225                 230                 235                 240

Ser Tyr Phe Ser Leu Thr Phe Leu Val Gln Thr His Gly Lys Asn Lys
                245                 250                 255

Asn Arg Arg Glu Lys Lys Tyr Glu Leu Phe Thr Asp Lys Thr Ser Ala
            260                 265                 270

Thr Val Ser Cys His Lys Ile Ser Lys Val Glu Val Arg Ala Arg Asp
        275                 280                 285

Arg Tyr Tyr Ser Ser Ser Trp Ser Glu Trp Ala Ser Val Ser Cys Ser
    290                 295                 300

Glu Val Ser Val Ser Arg
305                 310


<210> SEQ ID NO 41
<211> LENGTH: 305
<212> TYPE: PRT
<213> ORGANISM: Sigmodon hispidus

<400> SEQUENCE: 41

Ile Trp Glu Leu Glu Lys Asp Val Tyr Val Val Glu Val Asp Trp Ser
1               5                   10                  15

Pro Gly Ala Pro Gly Glu Arg Val Val Leu Thr Cys Asp Thr Ser Glu
            20                  25                  30

Glu Asp Asp Ile Ile Trp Thr Ser Asp Gln Ser Ser Glu Val Val Gly
        35                  40                  45

Ser Gly Lys Thr Leu Ile Val Gln Val Lys Glu Phe Ser Asp Ala Gly
    50                  55                  60

Gln Tyr Thr Cys His Lys Gly Gly Glu Thr Leu Ser His Ser Arg Leu
65                  70                  75                  80

Leu Leu His Lys Lys Glu Asp Gly Ile Trp Ser Thr Asp Ile Leu Lys
                85                  90                  95

Asp Gln Lys Asp Pro Lys Asn Lys Thr Phe Leu Lys Cys Glu Ala Ala
            100                 105                 110

Asn Tyr Ser Gly Arg Phe Thr Cys Trp Trp Leu Thr Ala Val Ser Thr
        115                 120                 125

Asp Leu Lys Phe Ser Leu Lys Ser Ser Ser Ser Ser Ser Asp Ser Arg
    130                 135                 140

Ser Val Thr Cys Gly Ala Ala Ser Leu Ser Thr Glu Lys Val Thr Val
145                 150                 155                 160

Asp Gln Arg Asp Tyr Asn Lys Tyr Ser Val Ala Cys Gln Glu Asp Ile
                165                 170                 175

Thr Cys Pro Thr Ala Glu Glu Thr Leu Pro Ile Glu Leu Val Met Glu
            180                 185                 190

Ala Gln His Lys Tyr Lys Tyr Glu Asn Tyr Ser Thr Gly Phe Phe Ile
        195                 200                 205

Arg Asp Ile Ile Lys Pro Asp Pro Pro Lys Asn Leu Gln Leu Lys Pro
```

-continued

```
    210                 215                 220

Leu Lys Ser Ser Gln Val Glu Val Ser Trp Glu Tyr Pro Asp Ser Trp
225                 230                 235                 240

Ser Thr Pro His Ser Tyr Phe Ser Leu Lys Phe Phe Val Gln Val Tyr
                245                 250                 255

Arg Lys Lys Glu Lys Lys Gly Glu Ser Leu Leu Val Asp Lys Pro Ser
            260                 265                 270

Ala Lys Ile Arg Cys Ser Lys Gly Gly Glu Val Arg Val Arg Ala Gln
        275                 280                 285

Asp His Tyr Tyr Asn Ser Ser Trp Ser Glu Trp Ala Ser Val Ser Cys
    290                 295                 300

Asn
305


<210> SEQ ID NO 42
<211> LENGTH: 313
<212> TYPE: PRT
<213> ORGANISM: Rattus norvegicus

<400> SEQUENCE: 42

Met Trp Glu Leu Glu Lys Asp Val Tyr Val Val Glu Val Asp Trp Arg
1               5                   10                  15

Pro Asp Ala Pro Gly Glu Thr Val Thr Leu Thr Cys Asp Ser Pro Glu
            20                  25                  30

Glu Asp Asp Ile Thr Trp Thr Ser Asp Gln Arg Arg Gly Val Ile Gly
        35                  40                  45

Ser Gly Lys Thr Leu Thr Ile Thr Val Arg Glu Phe Leu Asp Ala Gly
    50                  55                  60

Gln Tyr Thr Cys His Arg Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val His Arg Asn Thr Asp Leu Lys
        115                 120                 125

Phe Asn Ile Lys Ser Ser Ser Ser Ser Pro Glu Ser Arg Ala Val Thr
    130                 135                 140

Cys Gly Arg Ala Ser Leu Ser Ala Glu Lys Val Thr Leu Asn Gln Arg
145                 150                 155                 160

Asp Tyr Glu Lys Tyr Ser Val Ala Cys Gln Glu Asp Val Thr Cys Pro
                165                 170                 175

Thr Ala Glu Glu Thr Leu Pro Ile Glu Leu Val Val Glu Ala Gln Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Val Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Thr Lys Glu Thr Glu Glu Glu Cys Asn Gln Lys Gly Ala Phe
            260                 265                 270
```

```
Leu Val Glu Lys Thr Ser Ala Glu Val Gln Cys Lys Gly Ala Asn Ile
        275                 280                 285

Cys Val Gln Ala Gln Asp Arg Tyr Tyr Asn Ser Ser Cys Ser Lys Trp
    290                 295                 300

Thr Cys Val Pro Cys Arg Gly Arg Ser
305                 310


<210> SEQ ID NO 43
<211> LENGTH: 313
<212> TYPE: PRT
<213> ORGANISM: Mus musculus

<400> SEQUENCE: 43

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310


<210> SEQ ID NO 44
```

-continued

```
<211> LENGTH: 302
<212> TYPE: PRT
<213> ORGANISM: Artificial Sequence
<220> FEATURE:
<223> OTHER INFORMATION: synthetic: mature IL-12p40 having mutations
      outside the D3 region

<400> SEQUENCE: 44

Ile Trp Glu Leu Lys Lys Asp Val Tyr Val Val Glu Leu Asp Trp Tyr
1               5                   10                  15

Pro Asn Ala Pro Gly Glu Thr Val Val Leu Thr Cys Asp Thr Pro Glu
            20                  25                  30

Glu Asp Gly Ile Thr Trp Thr Ser Asp Gln Ser Ser Glu Val Leu Gly
        35                  40                  45

Thr Gly Lys Thr Leu Thr Ile His Val Lys Glu Phe Gly Asp Ala Gly
    50                  55                  60

Gln Tyr Thr Cys Arg Lys Gly Gly Glu Ala Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Ser Phe Leu Lys Cys Glu Ala Lys
            100                 105                 110

Asn Tyr Ser Gly Arg Phe Thr Cys Trp Trp Leu Thr Thr Ile Ser Thr
        115                 120                 125

Asp Leu Lys Phe Ser Val Lys Ser Ser Arg Gly Ser Thr Asp Pro Arg
    130                 135                 140

Gly Val Thr Cys Gly Thr Ala Thr Leu Ser Glu Asp Leu Gly Glu Tyr
145                 150                 155                 160

Lys Lys Tyr Arg Val Glu Cys Gln Glu Gly Ser Ala Cys Pro Ala Ala
                165                 170                 175

Glu Glu Ser Leu Pro Ile Glu Val Val Leu Glu Ala Val His Lys Leu
            180                 185                 190

Lys Tyr Glu Asn Tyr Thr Ser Ser Phe Phe Ile Arg Asp Ile Ile Lys
        195                 200                 205

Pro Asp Pro Pro Lys Asn Leu Gln Leu Lys Pro Leu Lys Asn Ser Arg
    210                 215                 220

His Val Glu Val Ser Trp Gly Tyr Pro Asp Thr Trp Ser Thr Pro His
225                 230                 235                 240

Ser Tyr Phe Ser Leu Thr Phe Cys Ile Gln Val Gln Gly Lys Ser Lys
                245                 250                 255

Arg Glu Lys Lys Asp Arg Ile Phe Thr Asp Lys Thr Ser Ala Thr Val
            260                 265                 270

Ile Cys Arg Lys Asn Ala Lys Ile Arg Val Gln Ala Arg Asp Arg Tyr
        275                 280                 285

Tyr Ser Ser Phe Trp Ser Glu Trp Ala Ser Val Ser Cys Ser
    290                 295                 300
```